(12) United States Patent
Ray Chaudhuri

(10) Patent No.: US 8,524,481 B2
(45) Date of Patent: Sep. 3, 2013

(54) HIDE PROCESSING METHODS AND COMPOSITIONS

(75) Inventor: Shaon Ray Chaudhuri, Kolkata (IN)

(73) Assignee: West Bengal University of Technology, West Bengal (IN)

( * ) Notice: Subject to any disclaimer, the term of this patent is extended or adjusted under 35 U.S.C. 154(b) by 0 days.

(21) Appl. No.: 13/321,316

(22) PCT Filed: Nov. 16, 2010

(86) PCT No.: PCT/IB2010/002845
§ 371 (c)(1),
(2), (4) Date: Nov. 18, 2011

(87) PCT Pub. No.: WO2012/017264
PCT Pub. Date: Feb. 9, 2012

(65) Prior Publication Data
US 2012/0142073 A1   Jun. 7, 2012

(30) Foreign Application Priority Data
Aug. 5, 2010   (IN) .............................. 863/KOL/2010

(51) Int. Cl.
*C12N 9/20* (2006.01)

(52) U.S. Cl.
USPC .................. 435/198; 435/253.3; 435/265

(58) Field of Classification Search
USPC ....................................... 435/198, 253.3, 265
See application file for complete search history.

(56) References Cited

U.S. PATENT DOCUMENTS

| | | | |
|---|---|---|---|
| 3,330,738 A | | 7/1967 | Napier, et al. |
| 4,978,619 A | | 12/1990 | Kajiwara et al. |
| 5,102,422 A | * | 4/1992 | Christner et al. ............... 8/94.15 |
| 6,708,531 B1 | | 3/2004 | Thanikaivelan et al. |
| 2004/0006825 A1 | | 1/2004 | Rose et al. |
| 2008/0220499 A1 | | 9/2008 | Nilegaonkar et al. |

FOREIGN PATENT DOCUMENTS
WO   WO-2010/043709   4/2010

OTHER PUBLICATIONS

Yadav, et al.., Purification and Chraterization of an Extracelluler protease from *Pseudomonas aeruginosa* isolated from east calcutta wetlans. J. Biol. Sci. 10 (5):424-431 (2010).*
Adarsh, V.K. et al., "Studies on Metal Microbe Interaction of Three Bacterial Isolates From East Calcutta Wetland," *OnLine Journal of Biological Sciences*, 2007, vol. 7, No. 2, pp. 80-88.
Ahmed, S.A. et al., "Stabilization of *Bacillus licheniformis* ATCC 21415 Alkaline Protease by Immobilization and Modification," *Aust. Journ. of Basic and Applied Sci.*, 2007, vol. 1, No. 3, pp. 313-322.
Aravindhan, R. et al., "A chemo-enzymatic pathway leads towards zero discharge tanning," *Journal of Cleaner Production*, Sep. 2007, vol. 15, pp. 1217-1227.

Betancor, L. et al., "Different mechanisms of protein immobilization on glutaraldehyde activated supports: Effect of support activation and immobilization conditions," *Enzyme and Microbial Technology*, 2006, vol. 39, pp. 877-882.
Chowdhury, S. et al., "Novel Metal Accumulator and Protease Secretor Microbes from East Calcutta Wetland," *American Journal of Biochemistry and Biotechnology*, 2008, vol. 4, No. 3, pp. 255-264.
Genbank Accession No. FJ788518 published Apr. 5, 2009, printed on Aug. 25, 2011, retrieved from internet at http://www.ncbi.nlm.nih.gov/nuccore/FJ788518, 1 page.
Genbank Accession No. GQ202011 published Sep. 11, 2009, printed on Aug. 25, 2011, retrieved from the internet at http://www.ncbi.nlm.nih.gov/nuccore/GQ202011, 1 page.
Govardhan, C.P., "Crosslinking of enzymes for improved stability and performance," *Curr. Opin. in Biotechnol.*, 1999, vol. 10, pp. 331-335.
Gupta, A. et al., "Purification and characterization of a solvent stable protease from *Pseudomonas aeruginosa* PseA," *J. Chromatography A.*, 2005, vol. 1069, pp. 155-161.
International Search Report and Written Opinion for PCT/IB2010/002845, mailed Mar. 21, 2011, 14 pp.
Karyakin, A.A. et al., "Self-doped polyanilines electrochemically active in neutral and basic aqueous solutions: Electropolymerization of substituted anilines," *J. Electroanalytical Chemistry*, 1994, vol. 371, pp. 259-265.
Kumar, S.R. et al., "Continuous production of L-glutaminase by an immobilized marine *Pseudomonas* sp BTMS-51 in a packed bed reactor," *Process Biochemistry*, 2003, vol. 38, pp. 1431-1436.
Mateo, C. et al., "Glyoxyl agarose: A fully inert and hydrophilic support for immobilization and high stabilization of proteins," *Enzyme and Microbial Technology*, 2006, vol. 39, pp. 274-280.
Morihara, K. et al., "Elastase Activity of some Purified Proteinase Preparations as Related to their Depilatory Action," *Agr. Biol. Chem.*, 1965, vol. 29, No. 9, pp. 836-839.
Najafi, M.F. et al., "Potential application of protease isolated from *Pseudomonas aeruginosa* PD100," *Electronic Journal of Biotechnology*, Aug. 15, 2005, vol. 8, No. 2, printed on Aug. 25, 2011, retrieved from internet at http://www.ejbiotechnology.info/content/vol8/issue2/full/5/5.pdf, 7 pages.
Ogino, H. et al., "Purification and Characterization of Organic Solvent-Stable Protease from Organic Solvent-Tolerant *Pseudomonas aeruginosa* PST-01," *Journal of Bioscience and Bioengineering*, 1999, vol. 87, No. 1, pp. 61-68.
Phadke, R.S., "Immobilization of enzymes/coenzymes for molecular electronics applications," *Biosystems*, 1995, vol. 35, pp. 179-182.
Rajput, A., "Enzymes and biotechnology for cleaner leather processing," *Current Science*, Jun. 10, 2009, vol. 96, No. 11, pp. 1439-1440.

(Continued)

*Primary Examiner* — Tekchand Saidha
*Assistant Examiner* — Rama P Ramanujam
(74) *Attorney, Agent, or Firm* — Foley & Lardner LLP

(57) ABSTRACT

Provided in part herein are compositions that include isolated microbial enzymes, such as proteases, lipases, useful in dehairing leather. Also provided are methods for isolating proteases, lipases, from microbes, as well as methods of reusing these enzymes effectively for several cycles in an environment friendly process.

40 Claims, 9 Drawing Sheets

(56) References Cited

OTHER PUBLICATIONS

Subba, R.C. et al., "Studies on Iproving the Immobilized Bead Reusability and Alkaline Protease Production by Isolated Immobilized *Bacillus circulans* (MTCC 6811) Using Overall Evaluation Criteria," *Appl. Biochem. Biotechnol.*, 2008, vol. 150, pp. 65-83.

Taylor, M.M. et al., "A Review of the Uses of Enzymes in the Tannery," *J. Am. Leather Chem. Assoc.*, 1987, vol. 82, pp. 153-165.

Thanikaivelan, P. et al., "Recent Trends in Leather Making: Processes, Problems and Pathways," *Critical Reviews in Environmental Science and Technology*, 2005, vol. 35, pp. 37-79.

Chaudhuri, S.R., et al., "Microbial genetic resource mapping of East Calcutta Wetland," *Current Science*, Jul. 25, 2006, vol. 91, No. 2, pp. 212-217.

Gauglhofer, J., "Environmental Aspects of Tanning with Chromium," *Journal of the Society of Leather Technologists and Chemists*, 1986, vol. 70, No. 1, 4 pp.

Ludvik, J., "The Scope for Decreasing Pollution Load in Leather Processing," US/RAS/92/120/11-51, Regional Programme for Pollution in the Tanning Industry in South-East Asia, United Nations Industrial Development Organization, Aug. 9, 2000, 36 pp.

Pvanakrishnan, R., et al., "Recent Advances in the Depletion of Hides and Skins," *Leather Science*, 1986, vol. 33, No. 76, pp. 177-191.

Rao, J. R., et al., "An eco-friendly option for less-chrome and dye-free leather processing: in situ generation of natural colours in leathers tanned with Cr-Fe complex," *Clean Technologies and Environmental Policy*, Sep. 2002, vol. 4, No. 2, pp. 115-121.

Saravanabhavan, S., et al., "Green solution for tannery pollution: effect of enzyme based lime-free unhairing and fibre opening in combination with pickle-free chrome tanning," *Green Chemistr*, 2003, vol. 5, The Royal Society of Chemistry, pp. 707-714.

\* cited by examiner

SEQUENCE LISTING

```
<160> NUMBER OF SEQ ID NOS: 5

<210> SEQ ID NO 1
<211> LENGTH: 484
<212> TYPE: DNA
<213> ORGANISM: Pseudomonas aeruginosa

<400> SEQUENCE: 1
gattgaacgc tggcggcagg cctaacacat gcaagtcgag cggatgaagg gagcttgctc      60
ctggattcag cggcggacgg gtgagtaatg cctaggaatc tgcctggtag tggggataa     120 cgtccggaaa cgggcgctaa taccgcatac gtcctgaggg agaaagtggg ggatcttcgg    180
acctcacgct atcagatgag cctaggtcgg attagctagt tggtggggta aaggcctacc    240
aaggcgacga tccgtaactg gtctgagagg atgatcagtc acactggaac tgagacacgg    300
tccagactcc tacgggaggc agcagtgggg aatattggac aatgggcgaa agcctgatcc    360
agccatgccg cgtgtgtgaa gaaggtcttc ggattgtaaa gcactttaag ttgggaggaa    420
gggcagtaag ttaataccct gctgttttga cgttaccaac agaataagca ccggctaact    480
tcgt                                                                 484
```

```
<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tactcgctgg gcaagttcag cg                                             22

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gtagctcatc accgaatagg cg                                             22

<210> SEQ ID NO 4
<211> LENGTH: 382
<212> TYPE: DNA
<213> ORGANISM: Pseudomonas aeruginosa

<400> SEQUENCE: 4
tttcccgcgc aggccagacc aagttgtcgc tgcaatcctg gtcggacgtc gccaagatca    60
acttcgtcga cgccggccag ggcgagcagg gcgacctcgt cttcggtaac ttcagcagca   120
gcgtcggcgg cgcggcgttc gctttcctgc cggatgttca ggatgcgctc aagggccagt   180
cctggtacct gatcaacagc agctacagcg ccaacgtcaa cccggccaat ggcaactacg   240
ggcgccagac gctgacccac gagatcggcc ataccctggg tctcagccac cccggcgact   300
acaacgccgg cgagggcgac ccgacctacg ccgacgccac ctacgccgag gacacccgcg   360
cctattcggt gatgagctac ca                                           382

<210> SEQ ID NO 5
<211> LENGTH: 482
<212> TYPE: DNA
<213> ORGANISM: Pseudomonas aeruginosa

<400> SEQUENCE: 5
gattgaacgc tggcggcagg cctaacacat gcaagtcgag cggatgaagg gagcttgctc    60
ctggattcag cggcggacgg gtgagtaatg cctaggaatc tgcctggtag tgggggataa   120
cgtccggaaa cgggcgctaa taccgcatac gtcctgaggg agaaagtggg ggatcttcgg   180
acctcacgct atcagatgag cctaggtcgg attagctagt tggtggggta aaggcctacc   240
aaggcgacga tccgtaactg gtctgagagg atgatcagtc acactggaac tgagacacgg   300
tccagactcc tacgggaggc agcagtgggg aatattggac aatgggcgaa agcctgatcc   360
agccatgccg cgtgtgtgaa gaaggtcttc ggattgtaaa gcactttaag ttgggaggaa   420
gggcagtaag ttaataccct tgctgttttga cgttaccaac agaataagca ccggctaact   480
tc                                                                 482
```

HIDE PROCESSING METHODS AND COMPOSITIONS

CROSS-REFERENCE TO RELATED APPLICATIONS

The present application is a U.S. national stage application of International Application No. PCT/IB2010/002845, filed on Nov. 16, 2010, which claims priority to Indian Patent Application No. 863/KOL/2010, filed Aug. 5, 2010, the entire contents of which are incorporated herein by reference in their entirety.

SEQUENCE LISTING

The instant application contains a Sequence Listing which has been submitted in ASCII format via EFS-Web and is hereby incorporated by reference in its entirety. Said ASCII copy, created on Oct. 13, 2011, is named 91619519.txt and is 2,924 bytes in size.

FIELD

The technology relates in part to isolated microbial lipases and proteases suitable for use in processing hides. The technology also relates in part to environmentally friendly dehairing processes.

BACKGROUND

Animal hides and skins have hair attached to them, and the hair often is removed in leather preparation processes. Leather preparation processes often involve use of toxic chemicals.

Natural microbial isolates may be used to produce enzymes, and these natural sources may be obtained from different environments. Urban areas sometimes dispose off waste in wetlands, and environmental samples from these waste dumps may contain a richly bio-diverse source of microbes. Enzymes from microbes can be utilized in leather preparation processes.

SUMMARY

Featured herein are methods, compositions, kits, and processes for processing hides. In one aspect provided is a hide dehairing process, including contacting a hide with a solution including a lipase and a protease for a predetermined amount of time, wherein the pH of the solution is substantially neutral; and removing hair from the hide. In some embodiments, the protease is a bacterial protease. In certain embodiments, the protease is from a gram positive bacteria. In some embodiments, the protease is from a gram negative bacteria. In some embodiments, the protease is a *Pseudomonas aeruginosa* secreted protease. In certain embodiments, the lipase is a bacterial lipase. In some embodiments, the lipase is from a gram positive bacteria. In certain embodiments, the lipase is from a gram negative bacteria. In some embodiments, the lipase is a *Pseudomonas aeruginosa* secreted lipase. In certain embodiments, the lipase is a *Pseudomonas aeruginosa* strain B/GZN (MTCC 5566) secreted lipase. In some embodiments, the method includes mechanically removing hair from the hide. In certain embodiments, the method includes scrubbing the hide. In some embodiments, the hide is contacted with the solution for 10 hours or more. In certain embodiments, the pH is about 7.5 to about 8.0. In some embodiments, the pH is about pH 8.0. In certain embodiments, the pH is about pH 7.5. In some embodiments, the solution comprises a bacterium that secretes the lipase. In certain embodiments, the solution comprises a bacterium that secretes the protease. In some embodiments, the bacterium is a *Pseudomonas aeruginosa* bacterium. In certain embodiments, the bacterium is a *Pseudomonas aeruginosa* strain A/SRC002 (MTCC 5564) bacterium. In some embodiments, the bacterium is a *Pseudomonas aeruginosa* strain B/GZN (MTCC 5566) bacterium. In certain embodiments, the bacterium is immobilized. In some embodiments, the bacterium is immobilized in a porous matrix. In certain embodiments, the bacteria cells cultured for enzyme activity are collected at late log phase of growth. In certain embodiments, the raw hide is salted. In some embodiments, the raw hide is dried. In some embodiments, the solution is maintained at a temperature of about 25 to 37 degree Celsius for the predetermined amount of time. In certain embodiments, the solution is applied to the hide by one or more of painting, dipping or spraying. In some embodiments, the solution is reusable. In certain embodiments, the solution is reusable for at least 7 cycles. In some embodiments, the solution is reusable for at least 20 cycles when obtained from immobilized cells. In some embodiments, the bacteria cells are immobilized in sodium alginate with calcium chloride. In certain embodiments, the bacteria cells are in a suspended culture. In some embodiments, the efficiency of the dehairing process is assessed by measurement of the tensile strength, softness, increase in square area, decrease in weight of the hide, or any combination thereof. In certain embodiments, the hide is an animal hide. In some embodiments, the hide is a rawhide. In certain embodiments, the predetermined amount of time is a time sufficient to remove the hair from the hide.

Also provided is a hide dehairing process, including contacting a hide with a solution including a lipase for a predetermined amount of time, where the pH of the solution is substantially neutral; and removing hair from the hide.

Also provided is a hide dehairing process, including contacting a hide with a solution including a *Pseudomonas aeruginosa* secreted protease for a predetermined amount of time, wherein the pH of the solution is substantially neutral; and removing hair from the hide. In some embodiments, the solution comprises a protease. In certain embodiments, the solution comprises a lipase. In some embodiments, the protease is a *Pseudomonas aeruginosa* strain A/SRC002 (MTCC 5564) secreted protease.

Also provided is a composition, including a solution including a lipase and a protease, wherein the pH of the solution is substantially neutral. In some embodiments, the composition includes a bacterium that secretes the lipase. In certain embodiments, the composition includes a bacterium that secretes the protease. In some embodiments, the composition includes a bacterium that secretes the lipase and a bacterium that secretes the protease.

Also provided is a composition, including a hide in contact with a solution including a lipase, where the pH of the solution is substantially neutral.

Also provided is a composition, comprising a hide in contact with a solution including a lipase and a *Pseudomonas aeruginosa* secreted protease, wherein the pH of the solution is substantially neutral.

Also provided is a culture consisting essentially of a *Pseudomonas aeruginosa* strain A/SRC002 (MTCC 5564) bacterium.

Also provided is a culture consisting essentially of a *Pseudomonas aeruginosa* strain B/GZN (MTCC 5566) bacterium Also provided is a kit for preparing a hide dehairing solution, including a culture of protease; and a culture of lipase. In some embodiments, the kit includes instructions for preparing a solution having a substantially neutral pH that contains (a) the protease secreted by a *Pseudomonas aeruginosa* strain A/SRC002 (MTCC 5564) and (b) the lipase secreted by a *Pseudomonas aeruginosa* strain B/GZN (MTCC 5566).

Also provided is a method of dehairing, a hide comprising: contacting a hide with a solution containing a protease for a predetermined incubation time, wherein soaking, degreasing and dehairing are performed in the incubation. In certain embodiments, the method includes a lipase.

In one aspect is provided a method that includes contacting a hide with a solution containing a protease for a predetermined incubation time, wherein soaking, degreasing and dehairing are performed in the incubation and the protease is described herein.

The foregoing summary illustrates certain embodiments and does not limit the disclosed technology. In addition to illustrative aspects, embodiments and features described above, further aspects, embodiments, and features will become apparent by reference to the drawings and the following detailed description and examples.

BRIEF DESCRIPTION OF THE DRAWINGS

The drawings illustrate embodiments of the technology and are not limiting. For clarity and ease of illustration, the drawings are not made to scale and, in some instances, various aspects may be shown exaggerated or enlarged to facilitate an understanding of particular embodiments.

DETAILED DESCRIPTION

Figure 1A:
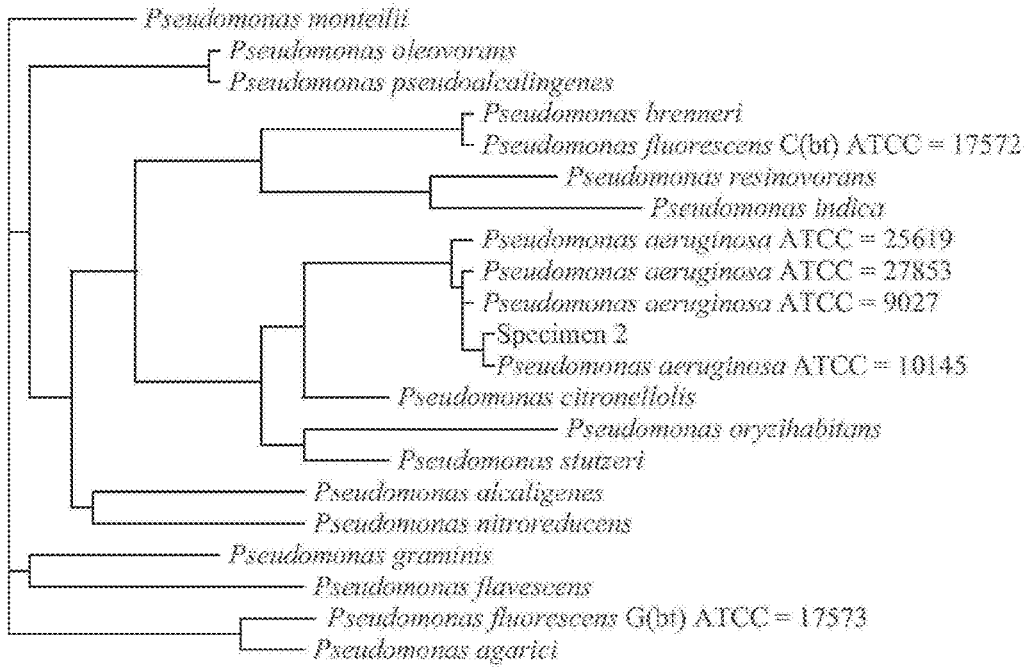
FIG. 1A provides an illustrative embodiment of a diagram of a phylogenetic tree based on the 16S rRNA gene sequence of the isolate SRC002 (MTCC 5564) constructed using the neighbor joining method.
Figure 1B:
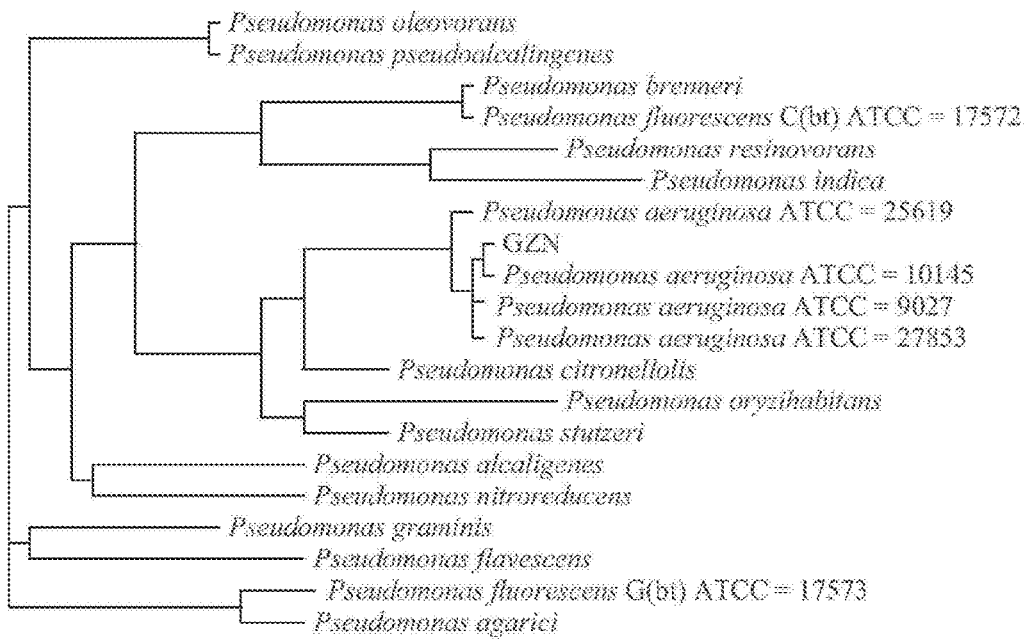
FIG. 1B provides an illustrative embodiment of a diagram of a phylogenetic tree based on the 16S rRNA gene sequence e of the isolate GZN (MTCC 5566) constructed using the neighbor joining method.

Microbial cultures described herein were deposited on May 2, 2010 at the Microbial Type Culture Collection and Gene Bank (MTCC), Sector 39-A, Chandigarh-160, 036, India, a Budapest Treaty recognized depository which affords permanence of the deposit. The cultures were accepted for deposit in MTCC-IDA under the Budapest Treaty and were accorded deposit numbers 5563, 5564, 5565, 5566, and 5567. Pursuant to the terms of the Budapest Treaty, the deposits of patent-protected strains will be made irrevocably publicly available upon patent grant.

In the following detailed description, reference is made to the accompanying drawings, which form a part hereof. In the drawings, similar symbols typically identify similar components, unless context dictates otherwise. Illustrative embodiments described in the detailed description, drawings, and claims do not limit the technology. Other embodiments may be utilized, and other changes may be made, without departing from the spirit or scope of the subject matter presented herein. It will be readily understood that aspects of the present disclosure, as generally described herein, and illustrated in the drawings, can be arranged, substituted, combined, separated, and designed in a wide variety of different configurations, all of which are explicitly contemplated herein.

General Aspects of Leather Production Processes

Leather may be used for a variety of diverse products such as, for example, clothing, body armor, boots, saddles, hunting accessories, weapons, roofs, tent coverings, containers, boat coverings, paper, dog chews, drum heads, book bindings, lacing, shoes, purses, gloves, luggage, coats, clothing accessories and the like. Leathers can be characterized and distinguished by flexibility, strength, water-resistant, softness, roughness, texture, preservability, weight, ventilation, evaporation characteristics, insulation and durability.

There are many distinct types of leather. While some are known for their strength and toughness, others are known for their softness. Full grain is produced from the top side of the leather or the outside of the skin, the surface will be smooth and polishable. Suede is produced from the underside of the skin and has a distinctive nap. The nap can be altered to be very fine, or long-almost hairy in appearance. Pigmented leathers have a light surface spray of color added at the final stage. This treatment produces a uniform appearance, useful for more formal shoes or leather goods. Nubuck is produced from full grain leathers, the grain is abraded to generate a light surface nap. This nap can be adjusted to be very fine, or a longer, softer effect can be produced.

Leather may be manufactured from hide obtained from a variety of different animals such as, for example, cow, calf, goat, deer, antelope, pig, crocodile, alligator, and ostrich.

Depending on the animal, the leather produced may differ in texture and use. For example, buck skin, or skin of a wild stag such as deer, elk or antelope, is useful for producing pliable leather with a smooth finish. Chamois, or sheepskin, is regarded for softness, absorbency and light tan color. This type of leather may be produced from skin of a goat-like animal. Suede may be generated when the reverse side of calfskin is roughened to obtain a soft product. Shoes, boots and jackets may be prepared with leather from the skin of full grown cows, which can be relatively tough and durable, and have a smooth or rough finish.

Printed leathers can have any type of pattern/design placed onto the surface. Designs often are embossed onto the leather surface under pressure and add to the character of the material, while the structure of the leather often is not affected. Oils and waxes often are coated onto the surface of the leather to produce a tacky finish that yields improved grip. Printed leathers often are used by athletes, e.g. American football gloves. Laminating leather to other materials can be utilized to generate a product having unique properties. The properties can be varied by selecting different laminates with characteristic properties.

Leather processing may start with any rawhide, pelt, hide, skin, fur, animal covering or the like, collectively referred to herein as a "hide." A hide may be from any suitable animal. Rawhide or pelt is a hide or animal skin that has not been exposed to tanning. It is similar to parchment, much lighter in color than leather made by traditional vegetable tanning. Hides are skins obtained from animals for human use. The skin may come from the soft outer covering of an animal, for example a vertebrate. A hide often includes hair, and hair with sufficient density is referred to as fur. Fur, the hair, or wool that covers an animal's skin often is stripped prior to or after a hide is provided.

Leather processing may generate several by-products that may be utilized. For example, meat, hair, organs, and bones from an animal, and the like, may be used for food, glue, gelatin, instruments, organ transplants, wigs, clothing, for example. Certain leather processing methods also can generate several by-products that have an impact on the environment. Leather preparation processes may involve the use of physicochemical and biological components. These procedures may include brine curing for preventing putrefaction of raw skins by bacteria or molds, soaking for removing components such as unneeded proteins and salts from raw skins, liming for producing limed pelt and removal of hair and proteins, deliming for removing lime, bating for biologically treating unneeded protein components and for surface cleaning, pickling for decreasing pH, neutralization, retanning, dyeing, fatliquoring. Most chemicals used in each step are discharged as wastewater after use in such processes. Such processes can employ chemicals such as sodium sulphide and lime, for example, which can lead to water pollution and soil pollution.

The term "dehairing" may refer to the removal of hair in any manner. Dehairing may also refer to the removal of fur or wool in any manner. Dehairing may be done by chemical, physical, or natural methods and combination thereof, for example. The term "remove" may means to take away, take off, detached, get rid of, do away with, move or shift from the original position or location or the like. For example, the removal of hair from a hide may mean that the hair may be detached entirely from the hide or still attached to the hide but loosened for ready removal by gentle scrubbing. Dehairing of a hide may occur at any time period and by any means Enzymes Enzymes can be used as alternatives to chemicals and can improve leather quality and reduce environmental pollution. Because enzymes often are active under moderate conditions, such as warm temperatures and neutral pH, they may reduce energy consumption by eliminating the need to maintain extreme environments required by many chemically catalyzed reactions. Reaction specificities of enzymes can minimize the amount of by-products produced in a leather preparation process, and therefore may offer a lower risk to the environment than chemically catalyzed reactions. Provided herein are eco-friendly applications of enzymes to leather manufacture processes, such as pre-tanning processes, for example.

In certain embodiments, enzymes, such as protease, lipase and/or amylase, are utilized. In some embodiments, a protease and lipase are used. In other embodiments, a lipase and an amylase are used. In certain embodiments, a protease and an amylase are used. Proteolytic, lipolytic and amylolytic enzymes may be derived from any suitable source, such as microbial, animal, yeast, mold and plant sources, for example. Enzymes also may be produced in large quantities and genetically manipulated to increase enzymatic activity. Enzymes, alone, or in combination, may be used in leather processing embodiments. The use of two or more enzymes may enhance the dehairing process in terms of time and/or quality of the final product.

Enzymes may be isolated and/or purified. Isolated enzymes may refer to separation from another or alone or solitary. Isolation may also refer to obtaining one or more enzymes in an uncombined or pure state or to set or place apart; detach or separate so as to be alone.

Purified enzymes may refer to making one or more enzymes pure; free from one or more or all things that debases, pollutes, adulterates, or contaminates. Purify may also refer to freeing from one or more or all foreign, extraneous, or objectionable elements. One or more enzymes may be isolated and/or purified by any means.

For example, if the enzymes are produced extracellularly by microbes, such enzymes/cells may be harvested from the culture. They may be harvested by centrifugation, for example, before the supernatant containing the enzymes is used for dehairing by incubation with the hides. Or the cells can be used directly without centrifugation/separation and direct incubation with the whole culture may be carried out to obtain similar results. Cells and/or enzymes may be purified and/or isolated. For example, the percentage of purification or isolation may be 20-30%, 25-35%, 30-40%, 35-45%, 40-50%, 45-55%, 50-60%, 55-65%, 60-70%, 65-75%, 70-80%, 75-85%, 80-90%, 85-95%, or 90-100%.

The ratio of enzymes used within the solution may be any ratio that efficiently dehairs the hides. For example, the ratio of two enzymes may be 1:1, 1:2, 1:3, 1:4, 1:5, 1:6, 1:7, 1:8, 1:9, 1:10, 2:3, 2:5, 2:7, 2:9, 3:4, 3:5, 3:7, 3:8, 3:10, 4:5, 4:7, 4:9, 4:11, 5:6, 5:7, 5:8, 5:9, 5:11, 6:7, 6:9, 6:11, 7:8, 7:9, 7:10, 7:11, 8:9, 8:11, 9:10, or 9:11. The ratio may be of lipase to protease, protease to lipase, protease to amylase, amylase to protease, lipase to amylase, or amylase to lipase or any combination thereof. The ratio of two ore more enzymes may be of any combination, such as for example, 1:1:1, 1:2:1, 1:2:2, !:3:1, 1:3:2, 1:4:1, :1:4:2, 1:5:1, 1:5:2, 1:6:2, 2:6:3 or the like. The ratio may be of lipase to two different proteases, a protease to two different lipases, a lipase, amylase and protease and the like or any combination thereof, for example.

The enzymes used may be contained in any manner necessary. For example, enzymes may be immobilized in a packed bed reactor to ensure continuous production of

Proteases

Proteases may be used for selective hydrolysis of non-collagenous constituents of the skins and for removal of proteins such as albumins, globulins, elastins and reticulins. Protease catalyzes the breakdown of proteins into small peptides and amino acids. The term "protease" includes proteins, polypeptides, and peptides having a protease activity, including a peptidase and/or a proteinase activity. Proteases can catalyze the hydrolysis of peptide bonds and may be cellular, secreted, or isolated. Proteases may optimally function in acidic, neutral or basic conditions. Many proteases have optimal activity under alkaline (basic) pH conditions. Proteases may function in a variety of pH conditions such as, for example, pH 1-4, 3-6, 5-8, 7-10, 6-8, 9-12 or 11-14. Proteases may also function in a variety of temperatures such as, for example, $-5$-$10°$ C., $0$-$5°$ C., $5$-$15°$ C., $10$-$25°$ C., $15$-$30°$ C., $25$-$40°$ C., $30$-$45°$ C., $40$-$55°$ C., $45$-$60°$ C., $55$-$70$, $60$-$75°$ C. and the like. Proteases may be divided into six or more groups, such as serine proteases, threonine proteases, cysteine proteases, aspartate proteases, glutamic acid proteases, and metalloproteases, for example.

Protease function may be inhibited by protease inhibitor enzymes, such as serpins, lipocalin proteins and the like. Proteases, being themselves proteins, can be cleaved by other protease molecules, sometimes of the same variety. Protease inhibitors, and sometimes multiple proteases, can be used in certain embodiments for regulation of peptidase activity.

A protease can be used in some embodiments for dehairing, bating and soaking, and for breaking down proteinaceous matter produced in processes described herein. Enzymes usefully provide advantages of specificity, stereospecificity, activity under mild conditions, possibility of producing 'natural' products, nonpolluting, and biodegradability.

Animal proteases and/or microbial proteases (e.g., from bacteria and/or fungi) sometimes are used in leather production processes (e.g., pre-tanning processes). Certain selection criteria include, in some embodiments, specificity, pH activity range as well as pH and thermal stability. Another criterion can be the ability of an enzyme to diffuse into a hide and/or skin, which can confer the ability of an enzyme to act substantially uniformly in a leather preparation process.

Neutral or alkaline proteases are utilized in some embodiments (e.g., obtained from bacteria or fungi), which have optimal activities at different pH points. Fungal proteases sometimes are classified according to pH activity range: fungal acid proteases act between pH 2.5 and 6.0 and can be derived from *A. satoi*. These can be used for bating prior to pickling and serve to open the fiber structure of hides. Fungal alkaline proteases belong to the same group of serine proteases as alkaline bacterial proteases. Fungal proteases often are more heat sensitive and are more quickly deactivated above 60° C. as compared to bacterial proteases. Fungal neutral proteases can be obtained from *Aspergillus* or *Penicillium* species.

Apart from bacterial and fungal proteases, specific proteases like keratinases are known. Keratinases which hydrolyse keratins, are obtained from *Streptomyces fradiae* and can be used for dehairing.

Lipases

A lipase can be used in leather processing to remove fats, oils, residues and the like. A lipase hydrolyzes triglycerides into mono and diglycerides, glycerol and free fatty acids which are more soluble than fats. The term "lipase" includes proteins, polypeptides, and peptides having a lipase activity. Lipases catalyze the hydrolysis of ester bonds in water-in-soluble, lipid substrates and may be cellular, secreted, or isolated. Lipases can enhance the color of leather and impart a cleaner appearance. Lipases may function in a variety of pH conditions such as, for example, pH 1-4, 3-6, 5-8, 7-10, 6-8, 9-12 or 11-14. Lipases may also function in a variety of temperatures such as, for example, $-5$-$10°$ C., $0$-$5°$ C., $5$-$15°$ C., $10$-$25°$ C., $15$-$30°$ C., $25$-$40°$ C., $30$-$45°$ C., $40$-$55°$ C., $45$-$60°$ C., $55$-$70$, $60$-$75°$ C. and the like.

Lipases may also be used (i) in the oil and fat industry to modify fats for use in foods; (ii) in detergent compositions; (iii) for fatty acid production, lipid synthesis via reversal of hydrolysis and lipid modification by interesterification, and (iv) in degreasing of hides and skins.

Amylases

An amylase catalyzes the break down of starch-based stains into smaller segments of oligosaccharides and dextrins that are water soluble. The term "amylase" includes proteins, polypeptides, and peptides having an amylase activity. Amylases catalyze the breakdown of starch, such as carbohydrates, into sugars. Amylases may be classified into three or more groups such as alpha, beta and gamma, for example. Amylases may be cellular, secreted, or isolated. Amylases may also contribute to the leather refining process used alone or in combination with other enzymes, additives, chemicals and the like. Amylases may function in a variety of pH conditions such as, for example, pH 1-4, 3-6, 5-8, 7-10, 6-8, 9-12 or 11-14. Amylases may also function in a variety of temperatures such as, for example, $-5$-$10°$ C., $0$-$5°$ C., $5$-$15°$ C., $10$-$25°$ C., $15$-$30°$ C., $25$-$40°$ C., $30$-$45°$ C., $40$-$55°$ C., $45$-$60°$ C., $55$-$70$, $60$-$75°$ C. and the like.

Amylase function may be inhibited by amylase inhibitor, such as phaseolamin, for example. Inclusion of such an amylase inhibitor in a process described herein may advantageously be used to regulate amylase activity.

Application of Enzyme Solution

The application of enzymes to hide may be performed in any suitable manner, non-limiting examples of which include drumming, painting, dipping, spraying and combinations thereof. In a paint method, an enzyme solution is mixed with an inert material (e.g., kaolin), made into a thin paste, adjusted to a predetermined pH, applied on the flesh side of a hide or skin, piled flesh to flesh, covered with polyethene sheets and maintained until dehairing takes place.

In a dip method, a hide or skin is immersed in an enzyme solution at a predetermined pH in a pit or tub. This method may include dilution of an enzyme solution. Even though enzyme penetration is observed as uniform, dehairing at backbone and neck sections may require more application of the solution and/or more time in solution.

An enzyme solution also may be sprayed onto a hide or skin. Advantages of spraying over painting and dip methods are (1) concentrated solutions can be sprayed, (ii) spraying an enzyme solution on the flesh side with force promotes access of the enzyme to the hide, (iii) backbone and neck can be sprayed with a great amount of enzyme, thereby making the dehairing process quicker, (iv) there is no effluent arising out of this method, and (v) after depilation, hair is substantially free from adhering skin tissues.

Microbes

Enzymatic dehairing is a reliable alternative to a conventional lime-sulphide step in leather processing. Using enzymes for dehairing as presented herein can provide advantages. Any enzyme from any type of microbe (e.g., bacteria) may be used alone or in combination.

The 16SrRNA gene may be used for phylogenetic studies as it is highly conserved between different species of bacteria and archaea. This gene may aid in characterizing and/or identifying different types of bacteria from one another. The 16S rRNA is a part of the ribosomal RNA—a 1542 nt long component of the small prokaryotic ribosomal subunit (30S). It is not possible for multiple sequences of the 16S rRNA to exist in a single bacterium. This subunit may have several functions. The large (23S) ribosomal RNA may serve a structural role, acting as a scaffold defining the positions of the ribosomal protein. The 3' end may contain the anti-Shine-Dalgarno sequence which may bind upstream to an AUG start codon on the mRNA. The subunit may also interact with the 23S subunit, aiding in the binding of the two ribosomal subunits (50S+30S).

The 16SrDNA of one or more bacteria may be similar to one another. For example, the 16SrDNA may be 95% or more, 90% or more, 85% or more, 80% or more, 75% or more, 70% or more, 65% or more, 60% or more, 55% or more, or 50% or more identical to another bacterium, for example. The 16SrDNA from one bacterium may also have 1, 2, or 3 nucleotide replacements, deletions or additions which may differ from another bacterium, for example.

Isolation/Selectivity

By "isolated" is meant that an enzyme, protein, polypeptide, or peptide, is substantially separated from other cellular materials. For example, a protein may be isolated from bacteria by being secreted into a supernatant, and the supernatant then separated from the protein-producing bacteria. Or, for example, a protein may be further purified using separation techniques that separate the protein from other materials in a composition. Isolated and/or purified bacteria may be from any genus and/or species. For example, bacteria may be from the genus *Pseudomonas, Aerobacter, Rhizobium, Rhizobiaceae, Agrobacterium, Bacillus, Clostridium, Nostoc, Trichodesmium, Xanthomonas, Nitrobacteriaceae, Nitrobacter, Nitrosomonas, Thiobacillus, Spirillum, Vibrio, Bacteroides, Escherichia, Klebsiella, Salmonella, Shigella, Erwinia, Rickettsia, Chlamydia, Mycoplasma, Actinomyces, Streptomyces, Mycobacterium, Polyangium, Micrococcus, Staphylococcus, Lactobacillus, Diplococcus, Streptococcus, Spirochaeta, Treponema, Borrelia*, or *Leptospira*. Bacteria may be from any species, which may be classified as spherical (cocci) or rod-shaped (bacilli) or spiral-shaped bacteria (spirilla). Isolated and/or purified bacteria may be from any species, such as, for example *Neisseria, Streptococcus, Staphylococcus, Actinobacteria*, or *Aeruginosa*

A microbial strain may be used to secrete enzymes by any available methods, including, for example, by batch fermentation and by immobilization of microbes. Fermentation can be conducted and controlled by various techniques. Appropriate nutrient cultures may be prepared, including, for example, carbon and nitrogen sources and other nutritional substances that favor or are necessary for the growth of the particular microbes (e.g., bacteria). Sugars and sugar-containing substances may be included as suitable sources of carbon, including, for example, but not limited to, starch, dextrin, cane sugar, lactose, maltose, fructose, and glucose. Nitrogen sources include, for example, protein-containing substances, such as peptone from soy beans, meat, casein, gelatin, yeast protein or yeast extract, wastes from the processing of meat or animal bodies, and ammonium salts. Other examples of nutrients include, for example, inorganic salts, for exampled alkaline and alkali earth metal salts and phosphates, together with trace elements, such as, for example, Fe, Mg, Mn, Co, and Ni.

Fermentation may be carried out at appropriate pH levels and temperatures to maximize microbe growth and secretion of enzyme, including, for example, at pH levels between about 5 and 9, or, for example, at pH levels between about 6 and 8. The temperature may be, for example, between about 33 to about 45 degrees Celsius, or, for example, between about 35 to about 39 degrees Celsius, or, for example, at about 37 degrees Celsius.

Bacterial growth and/or survival may depend on osmotic balance, carbon, nitrogen and or other growth conditions and/or factors. Bacteria are about 80-90% water and they require moisture to grow because they obtain most of their nutrients from their aqueous environment. Some types of bacteria, for example extreme or obligate halophiles, are adapted to—and require—high salt concentrations. In addition to water and the correct salt balance, bacteria may also require a wide variety of elements such as, for example carbon, hydrogen, and nitrogen, sulfur, ammonia, light, oxygen, phosphorus, potassium, iron, magnesium and calcium. Growth factors, such as vitamins and pyrimidines and purines may also be necessary. Bacteria may also grow or die in the presence of one or more antibiotics.

Immobilization

Any method, alone or in combination, listed below may be used to immobilize one or more of the enzymes. For industrial applications, the immobilization of enzyme on a solid support can offer additional advantages such as, but not limited to, repeated use of the enzyme, ease of product separation, and improvement in stability (Ahmed, S. A., et al., 2007. Stabilization of *Bacillus licheniformis* ATCC21415 alkaline protease by immobilization and modification, Aust. J. Basic Applied Sci., 1 (3): 313-322). For example, immobilization may include but is not limited to adsorption on glass, alginate beads or matrix (for example, see U.S. Pat. No. 4,978,619). One or more enzymes may be attached to the outside of an inert material, such as for example thiol enzymes, enzymes containing S—H groups near the active site (i.e. urease, dehydrogenase) or enzymes sensitive to gluteralolehyde and the like. Immobilization may be done in a variety of ways, for example, by physical retention such as an enzyme-coenzyme complex may be immobilized together having multipoint contacts between the enzyme and support such that the contact points are non-specific in an adsorption manner. Another immobilization method may be by chemical bonds, for example, from contact with an apoenzyme to form a holoenzyme. Other immobilization methods may employ other techniques, such as co-immobilization of inert proteins using serum albumin, (for example, Phadke. Immobilization of enzymes/coenzymes for molecular electronics applications, BioSystems 35 (1995) 179-182; Betancor, L et al. Different mechanisms of protein immobilization on glutaraldehyde activated supports: Effect of support activation and immobilization conditions, Enzyme and Microbial Technology Volume 39, Issue 4, 2 Aug. 2006, Pages 877-882; or Mateo, C. et al. Glyoxyl agarose: A fully inert and hydrophilic support for immobilization and high stabilization of proteins, Enzyme and Microbial Technology Volume 39, Issue 2, 26 Jun. 2006, Pages 274-280; Karyakin, A. A. et al.; or Self-doped polyanilines electrochemically active in neutral and basic aqueous solutions: Electropolymerization of substituted anilines, Journal of Electroanalytical Chemistry Volume 371, Issues 1-2, 27 Jun. 1994, Pages 259-265; Crosslinking of enzymes for improved stability and performance. Curr Opin Biotechnol. 1999 August; 10(4):331-5). Another immobilization method that may be used is entrapment where the enzyme is trapped in insoluble beads or microspheres, such as but not limited to calcium alginate beads. For example, entrapped cells in alginate beads allow the enzyme(s) to be secreted into the medium, where the enzyme in solution performs the function of dehairing, (see for example Najafi, M. F., et al., Potential application of protease isolated from *Pseudomonas*

*aeruginosa* PD100, Electronic Journal of Biotechnology, Vol. 8 No. 2, Aug. 15, 2005; or Subba Rao, C. Studies on Improving the Immobilized Bead Reusability and Alkaline Protease Production by Isolated Immobilized Bacillus circulans (MTCC 6811) Using Overall Evaluation Criteria. 2008, Electronic Journal of Biotechnology, Volume 150, 65-83). This method may also employ the use of spacer molecules such as but not limited to poly(ethylene glycol), for example.

Enzyme may also be produced using immobilized microbial cells, for example, as presented in Kumar, S. R. and M. Chandrasekharan, 2003 Continuous production of L-glutaminase by an immobilized marine *Pseudomonas* sp BTMS-51 in a packed bed reactor, Process. Biochem., 38: 1431-1436 and Samia A. Ahmed, Shireen A. Saleh and Ahmed F. Abdel-Fattah 2007 Stabilization of *Bacillus Licheniformis* ATCC 21415 Alkaline Protease by Immobilization and Modification Australian Journal of Basic and Applied Sciences, 1(3): 313-322, 2007. To reduce the production steps, immobilization of the cell may be performed by the protocol reported by Kumar et al. Modifications may include use of 8% Na-alginate solution and 1M $CaCl_2$. The beads were transferred to 25 ml of fresh medium and incubated at 37° C. overnight with continuous shaking. After each 24 hrs, the same beads were transferred to fresh medium as inoculum. After bead transfer, the overnight culture was used for dehairing. The efficiency of the enzyme may be checked each time by observing the hair removing performance and monitoring the units of enzyme secreted through hide powder assay. The process may be repeated as long as the beads are present.

Dehairing Efficiency

To assess the performance of one or more enzymes in a solution, enzyme efficiency may be measured in a variety of different manners. For example, the number of cycles a solution may be reused, the amount of time for soaking a hide, the toxicity of a solution after use, the color of a hide after soaking, the flexibility of a hide after soaking, the texture of a hide after soaking, the tensile strength of a hides after soaking, the softness of a hide after soaking, the temperature or pH of a solution during use, the number of hides that may be used per unit volume (e.g., cubic inch) of solution, effective enzyme concentration in a solution, the different body parts for hides that may be used for different concentrations of solution, the different concentrations of enzymes per solution, the amount of hair attached to the hides after soaking, the weight of the hides after soaking, the ease of hair removal after soaking and the like. Below are a few assays that may be used to assess enzyme and dehairing efficiency.

Soaking Parameters and Reuse

The hides may be soaked for any time period suitable for effectively dehairing a hide. For example, the hides may be soaked for about 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 hours, for example. The reusability of the solution containing one or more enzymes may ensure cost reduction involved in a continuous production. For example, the enzyme solution may be reused about 0, 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 times/cycles. An enzyme solution may be reused for about 0, 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 days, for example. The solution also may be "refreshed" with bacteria, and a predetermined ratio of new to old enzymes and/or bacteria may be utilized. For example, old to new or new to old bacteria and/or enzyme ratio may be 1:1, 1:2, 1:3, 1:4, 1:5, 1:6, 1:7, 1:8, 1:9, 1:10, 2:3, 2:5, 2:7, 2:9, 3:4, 3:5, 3:7, 3:8, 3:10, 4:5, 4:7, 4:9, 4:11, 5:6, 5:7, 5:8, 5:9, 5:11, 6:7, 6:9, 6:11, 7:8, 7:9, 7:10, 7:11, 8:9, 8:11, 9:10, or 9:11, for example. The "refreshing" step may occur in between each reuse of the solution or at every other reuse or every two reuses or every three reuses or every four reuses, for example.

Enzyme activity at neutral pH also ameliorates hazards associated with the released chemicals in relation to health of workers and the environment. The pH range of enzyme activity may be of any pH that efficiently dehairs the hides. For examples, the pH range may be pH 1-4, 3-6, 5-8, 7-10, 6-8, 9-12 or 11-14. Enzyme activity may also function in a variety of temperatures such as, for example, −5-10° C., 0-5° C., 5-15° C., 10-25° C., 15-30° C., 25-40° C., 30-45° C., 40-55° C., 45-60° C., 55-70, 60-75° C. and the like.

Leather Texture

Texture can be assessed in a variety of manners. Texture may include softness, brittleness, pliability, coarseness, stretchability, layers, smoothness, amount of grains, elasticity, weight, breadth, length, durability, longevity, and combinations thereof. Texture may be measured any known method such as, for example, by using instruments like a SMS MT-LQ Plus Texture Analyzer.

Tensile Strength

Tensile strength can be assessed in a suitable manner. In some embodiments, tensile strength can be determined by the maxima of a stress-strain curve and, in general, indicates when necking or deformation can occur. As tensile strength is an intensive property, its value may not depend on the size of the test specimen. It is, however, dependent on the preparation of the specimen and the temperature of the test environment and material. An increase in hide length and breadth may indicate an increase in tensile strength of the hide. The tensile strength is measured by any known method, such as, for example, using tensile testers, crackness tester, and/or two dimensional extension testers.

Softness

The softness of a hide may be determined by any known method, such as touch, indentation, compression, reformation, resistance, pliability, comparing, consistency, consistent repetition, consistent durability, smoothness, flexibility, amount of grains that can be felt, weight, length, layers, coarseness and the like. Use of instruments such as the ST300 softness tester, may also be used.

EXAMPLES

The examples set forth below illustrate certain embodiments and do not limit the disclosed technology.

Example 1

Protease Isolation

A particular protease enzyme was isolated from a bacterial culture (Strain A/SRC002 (deposited with the Microbial Type Culture Collection & Gene Bank, Sector 39-A, Chandigarh-160 036, India on May 24, 2010 and assigned reference number MTCC 5564)) and used as part of a leather processing method. Strain A was obtained from water sample collected from Charakdanga Bheri, a waste water fed fishery which is an integral part of East Calcutta Wetland. Location map indicates 22°32' 04.95" N and 88°24' 21.70" E (Using Google Earth http://earth.google.com/). It is a gram negative bacillus that produces protease, catalase, DNAse, lipase, oxidase, but does not secrete lecithinase. The molecular identification of the isolate was based on partial sequence analysis of 16SrDNA. This partial sequence shows 100% identity with *Pseudomonas aeruginosa*.

```
                                                         (SEQ ID NO: 1)
GATTGAACGCTGGCGGCAGGCCTAACACATGCAAGTCGAGCGGATGAAGG

GAGCTTGCTCCTGGATTCAGCGGCGGACGGGTGAGTAATGCCTAGGAATC

TGCCTGGTAGTGGGGGATAACGTCCGGAAACGGGCGCTAATACCGCATAC

GTCCTGAGGGAGAAAGTGGGGGATCTTCGGACCTCACGCTATCAGATGAG

CCTAGGTCGGATTAGCTAGTTGGTGGGGTAAAGGCCTACCAAGGCGACGA

TCCGTAACTGGTCTGAGAGGATGATCAGTCACACTGGAACTGAGACACGG

TCCAGACTCCTACGGGAGGCAGCAGTGGGGAATATTGGACAATGGGCGAA

AGCCTGATCCAGCCATGCCGCGTGTGTGAAGAAGGTCTTCGGATTGTAAA

GCACTTTAAGTTGGGAGGAAGGGCAGTAAGTTAATACCTTGCTGTTTTGA

CGTTACCAACAGAATAAGCACCGGCTAACTTCGT
```

The bacteria is resistant to Cephotaxime, Ampicillin, Tetracyclin, PolymyxinB, Cloramphenicol, Ceftazidime, Cloxacillin, Gentamycine, Rifampicin, Doxycycline hydrochloride, Cephadroxil, Vancomycin, Metronidazole, Trimethoprim. Resistance was tested to be completely resistant (100%).

The sensitivity of the strains against different antibiotics was determined by disk diffusion method using commercially available (Himedia) antibiotic discs. The representative of each group of antibiotic had been tested. The antibiotics used were Ampicillin (A10), Cephadroxil (Cq30), Chloramphenicol (C30), Cloxacillin (Cx30), Cephotaxime (Ce30), Ceftazidime (Ca30), Ciprofloxacin (Cf5), Doxycycline Hydrochloride (Do30), Gentamicin (G10), Metronidazole (Mt4), Neomycin (N30), Norfloxacin (Nx10), Polymyxin B (Pb100), Rifampicin (R15), Roxithromycin (Ro30), Tetracycline (T30), Trimethoprin (Tr30), Vancomycin (Va30). The concentrations of the antibiotics in microgram per disc were mentioned in parenthesis indicated above except for Polymyxin B where it is 100 units. Mueller Hinton Agar medium (Himedia-M173) was used to grow each of the microorganisms for antibiotic sensitivity test. The log phase culture of each isolate was diluted 100 times and poured on Mueller Hinton Agar (MHA) plates. It was swirled uniformly to distribute the culture throughout the plate. After waiting for 30 mins, the cultures were carefully pipetted out from the plates and the plates were allowed to dry. Then the antibiotic disks were placed onto the MHA surface using the dispenser provided with the antibiotic discs. The plates were incubated at 37° C. for overnight. The zones of inhibition were measured. The results were evaluated using National Committee for Clinical Laboratory Standard's (NCCLS) chart provided with the antibiotic discs by Himedia. The assay was repeated three times for each organism.

The bacteria is sensitive to Ciprofloxacin, Neomycine and Norfloxacine. Selective screening of Strain A was performed in milk medium (0.3% yeast extract, 10% milk; 1.5% agar) and Luria Bertani broth (1% tryptone, 0.5% yeast extract, 0.5% sodium chloride). For cultivation jaggery, an unrefined non centrifugal sugar obtained as a concentrated product of cane juice without separation of mollasses and crystals, also was used.

The isolate was found to grow in the presence of heavy metal salts such as Pb, Cr, Cd, Hg, Cu, Ni, and Cd. Strain SRC002 (MTCC 5564) showed about 500 ppb accumulation of lead. Strain SRC002 (MTCC 5564) showed distinct nanoparticles of Pb, Cr, Cd, Hg and Cu post-treatment. As an effect of metal induced stress, distinct changes were observed in cell morphology. Strain SRC002 (MTCC 5564) demonstrated generation of wooly coat post Ni treatment, while cell elongation was observed in case of Cd treatment.

Under submerged fermentation conditions, the optimum time of protease and lipase production (e.g., see Example 2 for lipase production) was determined on the basis of enzyme activity. The culture was collected at late log phase of growth (with optimum protease activity) and different parts of hide (2×2 cm) were dipped in separate sets for 10 hours. A conventional process was also applied on hides from different parts for the same time period. In order to make the process cost efficient, the medium formulation was modified by replacing the Luria Bertani enriched medium with jaggery.

Sequencing of the apr gene reflected the enzyme to be a member of the alkaline protease family according to the sequence comparison.

Procedure: Genomic DNA was isolated from the strains by a modified alkali lysis method. PCR amplification of the aprA gene fragments was done using the aprA-specific primer set for *Pseudomonas aeruginosa* (5'-TACTCGCTGGGCA AGTTCAGCG-3' (SEQ ID NO: 2) and 5'-GTAGCT CAT-CAC CGAATAGGCG-3' (SEQ ID NO: 3)) under the following conditions: initial denaturation at 94° C. for 5 min; 35 amplification cycles (denaturation at 94° C. for 30 s; annealing at 59° C. for 30 s; extension at 72° C. for 30 s); and a final post-extension at 72° C. for 5 min (Kim et al, 2006). After PCR the amplicon was run on a 2% agarose gel with a 100 by DNA ladder (Cat. No. SM0623, Fermentas), and then stained with ethidium bromide. The PCR product of 400 base pair once confirmed on the gel was sent for partial sequencing. The sequence was subjected to blast analysis, and also submitted to GenBank under the accession number GQ202011 (Adarsh V K, Madhusmita Mishra, Sanhita Chowdhury, M Sudarshan, A. R. Thakur and S Ray Chaudhuri. 2007 Studies on metal microbe interaction of three bacterial isolates from East Calcutta Wetland. Online Journal of Biological Sciences, 7(2):80-88).

```
                                              (SEQ ID NO: 4)
Gene sequence:-
tttcccgcgc aggccagacc aagttgtcgc tgcaatcctg gtcggacgtc gccaagatca acttcgtcga cgccggccag ggcgagcagg gcgacctcgt cttcggtaac ttcagcagca gcgtcggcgg cgcggcgttc gctttcctgc cggatgttca ggatgcgctc aagggccagt cctggtacct gatcaacagc agctacagcg ccaacgtcaa cccggccaat ggcaactacg ggcgccagac gctgacccac gagatcggcc atccctggg tctcagccac cccggcgact acaacgccgg cgagggcgac ccgacctacg ccgacgccac ctacgccgag gacacccgcg cctattcggt gatgagctac ca
```

SDS PAGE analysis of the extracellular supernatant from strain SRC002 (MTCC 5564) showed two bands, one between 66 and 43 kD and another between 43 and 29 kD. Purified protein obtained after hydrophobic interaction chromatography was homogeneous on SDS-PAGE. Its molecular weight was estimated to be around 35 kD, which is different from other reported proteases (18 to 49 kD). The dehairing was performed with crude extracellular protease. To understand the enzyme better the purification was performed as per the protocol mentioned below:

Purification: 200 mg of protein mixed with a binding buffer (20 mM phosphate buffer pH-7.0 with 50% ammonium sulphate) obtained by concentrating extracellular supernatant using speedvac for 30 hours was loaded onto a Phenyl Sepharose CL-4B column pre-swollen in 20% ethanol (3.8 cm length, 1.8 cm diameter, bed volume 9.66 ml), pre-equilibrated with 20 mM phosphate buffer (pH-7.0), at a flow rate of 1.5 ml/min. The column was washed with the same buffer. The bound enzyme was then eluted with a stepwise gradient of ammonium sulfate (50-0% concentration) in 20 mM phosphate buffer (each gradient was of 20 ml). Total volume of elution was 100 ml. Fractions of 5 ml were collected, protein content and protease activity of each fraction was measured. The fractions showing activity were dialyzed extensively against 20 mM phosphate buffer (pH-7.0) to remove ammonium sulphate. The characterization of the active fraction was done. ESI Mass Spectroscopy was also done for exact enumeration of the molecular weight of the purified protein.

Activity gel protocol: The zymograph of extracellular supernatants from all the strains showed distinct activity with gelatin as substrate on a renatured SDS PAGE gel in the case of SRC-002 and SRC-004. SRC-005 also gave a very faint band in gelatin containing SDS zymograph. Though the other isolates showed activity on milk media plate (plate clearing activity) as well as during biochemical assay with hide powder azure and azocasein, they failed to show activity on the zymograph indicating absence of gelatinase activity. The enzyme might be composed of multiple subunits of variable molecular weights which may have been separated on the SDS PAGE, thus not showing activity. It was also possible that these proteins needed some cofactors which were displaced on SDS PAGE and thus resulting in loss of activity.

Analysis also showed a clearing zone in the activity gel containing gelatin as a substrate: the upper band which was present in the crude extracellular supernatant did not show a clearing zone in the activity gel. The molecular weight of the purified protein was further confirmed as 36.18 kDa by ESI Mass Spectroscopy.

The protease content of cell free supernatant was determined by a protease assay using hide powder azure as substrate as discussed in Chowdhury, S., et al., 2008, *Novel Metal Accumulator and Protease Secretor Microbes from East Calcutta Wetland*, American Journal of Biochemistry and Biotechnology 4: 255-264, which is incorporated herein by reference.

Enzyme kinetics study revealed the presence of two isozymes of the protease or two different protease enzymes. One of the enzymes acts at low substrate concentration while the other was found to be active at higher substrate concentration. The Km value of these two protease, determined from Lineweaver-Burk plots, were 18.18 and 46.5 mg/ml.

Figure 2:
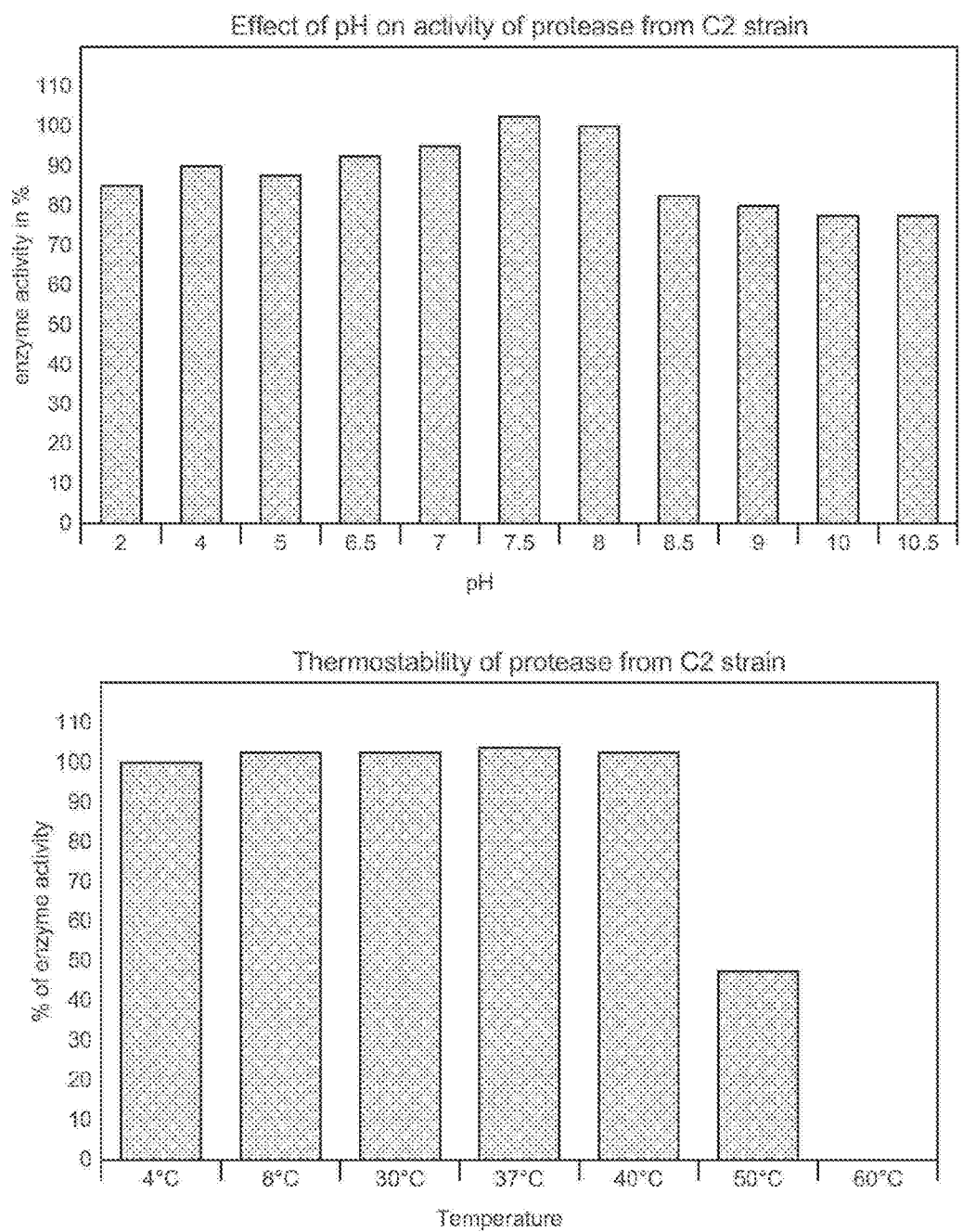
FIG. 2A is a bar graph of an illustrative embodiment of the pH profile of the protease enzyme from strain SRC002 (MTCC 5564).
FIG. 2B is a bar graph representing an illustrative embodiment of the thermo stability of protease from strain SRC002 (MTCC 5564).

The enzyme activity was marked over the entire temperature range of 4° C. to 50° C., and 4° C. to 40° C., with maximum activity at 40° C. (FIG. 2B). This optimum temperature is lower than values reported for other proteases from *P. aeruginosa* strains (Ogino, H., F. Watanabe, M. Yamada, S. Nakagawa, T. Hirose, A. Noguchi, M. Yasuda, and H. Ishikawa. 1999. Purification and characterization of organic solvent-stable protease from organic solvent-tolerant *Pseudomonas aeruginosa* PST-01. J. Biosci. Bioeng. 87:61-68 and Gupta A., Roy I., Khare S. K., Gupta M. N., 2005. Purification and characterization of a solvent stable protease from *Pseudomonas aeruginosa* PseA. J. Chromatogr. 1069, 155-161. [doi 10.1007/s00253-002-0975-y]).

EGTA (10 mM); 1,10 Phenanthrolin (2 mM), and Phosphoramidone (500 µg/ml) completely inhibited protease activity. Antipain (20 µM); Bestatin (50 µg/ml); Chymostatin (20 µM); E-64 (2 µM); Pepstatin (1 µM) and Ebelacetone-B (1 µM) had almost no effect on the activity of the protease.

The enzyme depicted more than 80% activity within a wide range of pH from 3-10.5, maximum activity being at a neutral range of 7.5-8 (FIG. 2a). Other proteases from *P. aeruginosa* are reported to exhibit optimum pH values ranging from 7 to 9. The pH profile of the crude enzyme showed almost similar activity along the entire range of pH 5-8 with an optimum at pH 7. The activity of the enzyme at neutral pH can reduce problems arising due to alkalinity caused by lime application.

The enzyme retained up to 90% activity in the presence of Cr, 82% in the presence of Co, 76% in the presence of Ag, 70% in the presence of Ni and Al, 50% in the presence of Pb and Cu, and 34% in the presence of Zn and Cd with complete inhibition in the presence of Hg. EDTA also inactivated the enzyme activity, while beta-merceptoethanol, hydrogen peroxide, Triton X 100, bleach, and detergent partially inhibited the activity of the crude enzyme. Likewise EGTA, 1, 10 phenanthrolin and phosphoramidone completely inhibited protease activity, while Antipain, Bestatin, Chymostatin, E-64, Pepstatin and Ebelacetone-B had no inhibitory effect.

Example 2

Lipases

A particular lipase enzyme was isolated from a bacterial culture (Strain B/GZN (deposited with the Microbial Type Culture Collection & Gene Bank, Sector 39-A, Chandigarh-160 036, India on May 24, 2010 and assigned reference number MTCC 5566)) and used as part of a leather processing method. The source of Strain B was a soil sample from the so-called "green zone," which is the oldest dumping ground that is currently used as a recreational center with a forest like ecosystem. Location map indicates 22°32' 17.5" N and 88°23' 53.7" E (Using Google Earth http://earth.google.com/).

| Isoate | Site of isolation | Colony Morphology | | | | | |
|---|---|---|---|---|---|---|---|
| | | Size | Margin | Elevation | Texture | Light transmission | Pigment/Colour |
| GZN | Green Zone (soil) | 0.8-1 cm | Erose, filamentous | Flat | Shiny, mucoid | Opaque | Green |

This is the oldest dumping ground which received waste from throughout the city; at present named Green one. The climate is overall hot and humid over the year.

It is gram negative. The molecular identification of the isolate was based on a partial sequence analysis of 16SrDNA, and the sequence is available at GenBank as GZN with the accession number FJ788518.

(SEQ ID NO: 5)
```
gattgaacgc tggcggcagg cctaacacat gcaagtcgag cggatgaagg gagcttgctc ctggattcag cggcggacgg gtgagtaatg cctaggaatc tgcctggtag tgggggataa cgtccggaaa cgggcgctaa taccgcatac gtcctgaggg agaaagtggg ggatcttcgg acctcacgct atcagatgag cctaggtcgg attagctagt tggtggggta aaggcctacc aaggcgacga tccgtaactg gtctgagagg atgatcagtc acactggaac tgagacacgg tccagactcc tacgggaggc agcagtgggg aatattggac aatgggcgaa agcctgatcc agccatgccg cgtgtgtgaa gaaggtcttc ggattgtaaa gcactttaag ttgggaggaa gggcagtaag ttaataccett gctgttttga cgttaccaac agaataagca ccggctaact tc
```

This partial sequence shows 100% identity with *Pseudomonas aeruginosa*.

The strain produces protease and lipase and is Vancomycin, Ampicillin, Polymyxin B, Ciprofloxacillin, Norfloxacillin, Doxycycline, Tetracycline, and Rifampicin resistant.

The strain is also sensitive to gentamycin and shows intermediate response to neomycin, cefotaxime, ceftazidime, trimethoprim, and chloramphenicol. The strain does not secrete protease, catalase, oxidase, DNase, lecithinase or amylase. The production of enzyme was quantified by a spectrophotometric method using pNPP as substrate. It was found that strain B produces about 3 units of lipase after 16 hours of growth.

The isolate was found to grow in the presence of heavy metal salts such as Pb. Strain GZN (MTCC 5566) showed about 2688 ppb of intracellular accumulated lead. After treatment, the strain had accumulation of metals such as Cu and Ag. As an effect of metal induced stress, distinct changes were observed in cell morphology. Isolated GZN (MTCC 5566) strains showed distinct shortening in cell size post treatment with heavy metals such as Al, Cr, Fe, Pb and Ag.

Enzyme production was optimized in flask culture. For strain B, minimal (Carbon minimal salt) medium with coconut oil as substrate was used as selective medium; Luria Bertani broth was used for cultivation. For cultivation jaggery, an unrefined non centrifugal sugar obtained as a concentrated product of cane juice without separation of mollasses and crystals, was also used.

| Biochemical Characterization | | | | | | |
|---|---|---|---|---|---|---|
| Isolate | Catalase | Oxidase | DNase | Protease | Lipase | Lecithinase |
| GZN | + | + | + | + | + | − |
| Optimum pH | | | | 6 | | |
| Optimum temperature | | | | 37-40° C. | | |

Example 3

Dehairing Solution

A culture of the microbes described above was directly used in a one step incubation of about 10 hours, that combined the conventional steps of soaking, degreasing and dehairing, resulting in a faster processing time. In this example, there was also a reduction in time and monetary expenditure in processing the leather due to omitting of cell harvesting as well as combining the three pretanning processes into one.

The two isolates of *Pseudomonas* species from East Calcutta Wetland (different locations) Strain A (described in Example 1) and strain B (described in Example 2) were used Both the isolates were found to grow under a wide range of temperature as well as pH, as described herein. This tolerance provides an advantage of utilization under different environmental conditions. Goat raw hides were soaked in the lipase and protease (about a 1:1 proportion) containing solution for a period of about 10 hours at room temperature (30° C. to 35° C.) and at neutral pH range. After the incubation, the hides were gently scrubbed and washed in water, which resulted in removal of hair. The hair byproduct can be commercially used for brush production or the like.

The ratio of enzymes used within the solution may be any ratio that efficiently dehairs the hides. For example, the ratio may be 1:1, 1:2, 1:3, 1:4, 1:5, 1:6, 1:7, 1:8, 1:9, 1:10, 2:3, 2:5, 2:7, 2:9, 3:4, 3:5, 3:7, 3:8, 3:10, 4:5, 4:7, 4:9, 4:11, 5:6, 5:7, 5:8, 5:9, 5:11, 6:7, 6:9, 6:11, 7:8, 7:9, 7:10, 7:11, 8:9, 8:11, 9:10, or 9:11. The ratio may be of lipase to protease, protease to lipase, protease to amylase, amylase to protease, lipase to amylase, or amylase to lipase.

Example 4

Cycling of Immobilized Cells for Enzyme Production

Reusability of the culture containing enzyme advantageously reduces the cost of continuous production. An overnight bacterial culture was grown and used for incubation of raw hide. After incubation for 10 hours, the treated hide was removed and a fresh hide was placed in the culture. The loss in volume of the used culture may be made up by addition of adequate growth media. It may be used continuously for about 7 consecutive cycles with equal efficiency.

Figure 7:
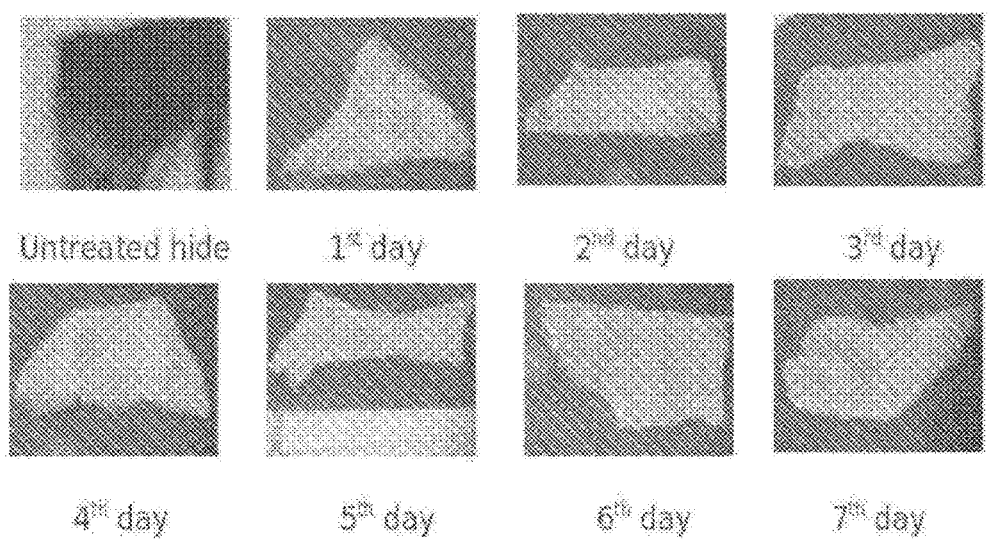
FIG. 7 provides illustrative photographs of the reusability of the cell culture containing extracellular protease.
Figure 8:
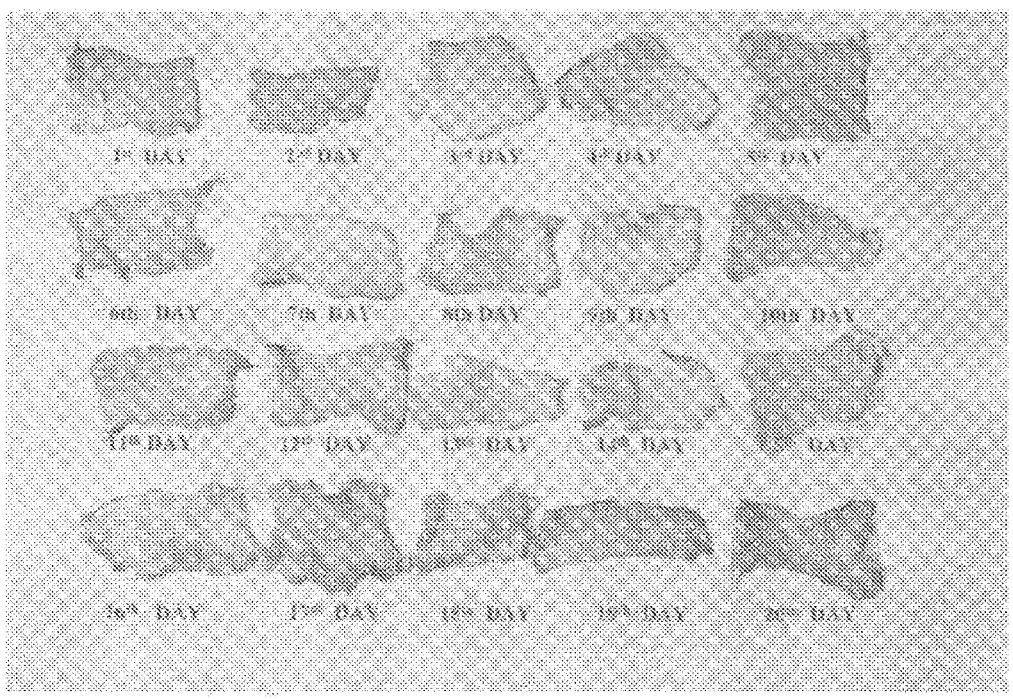
FIG. 8 provides illustrative photographs of the dehairing by the enzymes from immobilized cells.

The efficiency of protease enzyme in dehairing was assessed under suspension and immobilization conditions. Repeated use of the same starter culture made the entire process more cost effective. In the suspension culture, recycling was performed for 7 cycles, and each cycle exhibited about the same dehairing efficiency (FIG. 7). Under immobilized conditions (1% inoculum in 8% sodium alginate and 1 M CaCl$_2$ (modified protocol of Kumar et al, see Example 5)), it was determined that dehairing was efficient for 20 cycles (FIG. 8). The enzyme activity was found to be about same until the 20th cycle (FIG. 8). For the lipase producing strain, the reusability was also found to be efficient. The immobilization in a packed bed reactor ensured continuous production of enzyme over an extended period.

Example 5

Immobilization of Cells and Packed Bed Method for Enzyme Production

For immobilization in alginate beads, cells were immobilized using a protocol adapted from Kumar and Chandrasekharan (2003, Continuous production of L-glutaminase by an immobilised marine *Pseudomonas* sp BTMS-51 in a packed bed reactor, Process Biochem., 38: 1431-1436) with some modification (e.g., 8% Na-alginate solution and 1M $CaCl_2$ were utilized). A concentrated cellular suspension was mixed with 8% Na alginate solution and added drop wise into chilled calcium chloride solution to form beads. The bead solution was kept chilled until transferred into medium following a PBS wash to remove additional calcium chloride solution. The beads then were transferred to 25 ml of fresh medium, and incubated at 37° C. overnight with continuous shaking. After each 24 hr period the same beads were transferred to fresh medium as the inoculum. After transferring the beads, the overnight culture was used for dehairing. The efficiency of the enzyme solution was checked each time by observing the hair removal performance, and by monitoring the units of enzyme secreted using the hide powder assay.

The process was repeated so long as the beads were present. As the incubation proceeds the beads slowly start disrupting/dissolving in the incubating medium. The process may be continued so long as even small numbers of beads are present.

For packed bed based production the following method was adopted:

Rice straw (or any similar matrix) of any type was cut into small pieces (roughly 2 to 3 cm long) and boiled for about 5 minutes. Then the water was decanted and fresh water was added. The entire process was repeated about 3 to 4 times till no color was further seen in the boiled water to ensure complete removal of any nutrients.

It was then dried at 37° C.

Figure 9:
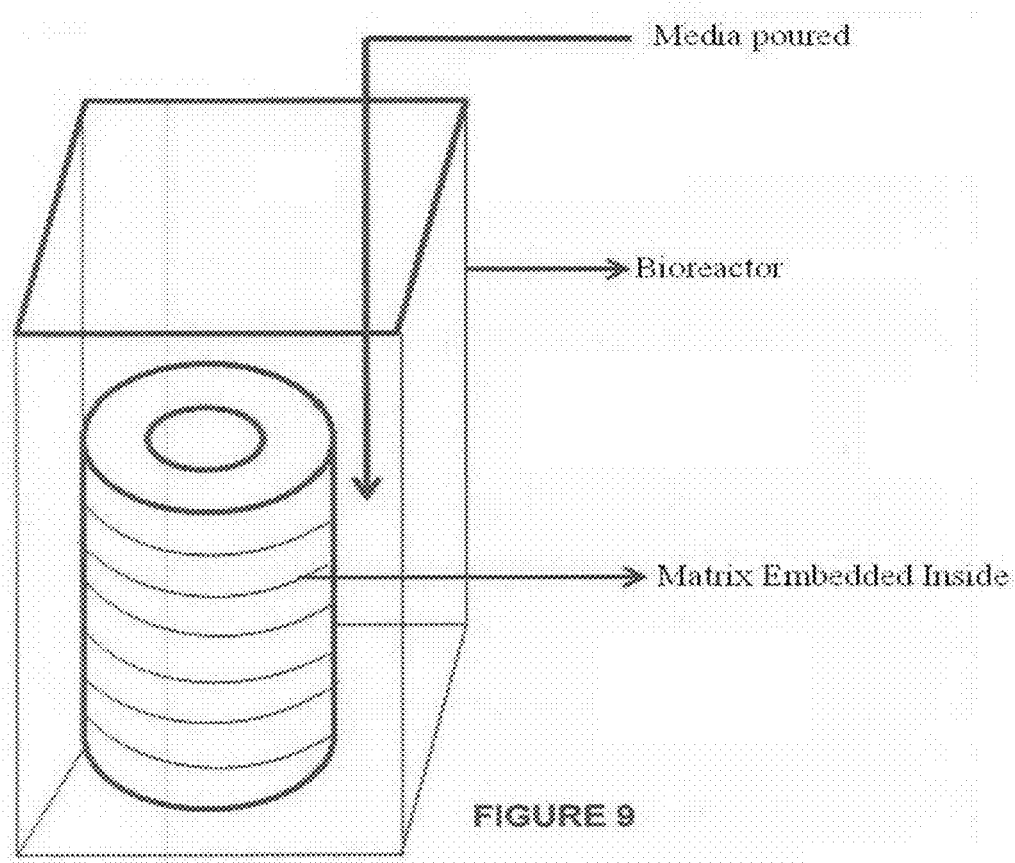
FIG. 9 provides an illustrative photograph of a bioreactor column.

The column of the bioreactors was filled with straw to act as a matrix for cell growth. Any other similar type of matrix may also be used. The bioreactor column may be a plastic case with perforations on the wall that would enable the medium to move in and out of the column. See FIG. 9.

200 ml L.B broth was prepared in a conical flask, sterilized, and inoculated with 2 ml of the culture of the desired strain.

The flask was incubated at 37° C. for overnight.

The overnight grown culture was poured into a chamber containing the column so as to allow the cells and culture media to perfuse the bioreactor matrix. The bacteria in the culture adhere to the boiled straw using it as a matrix for immobilization and biofilm formation. The chamber is filled with the culture media to ensure that the straw inside the column stays in contact with the bacteria in the culture media for 24 hours.

The chamber including the bioreactor column was kept for 24 hrs at room temperature.

After 24 hours, the culture media was decanted from the chamber and bioreactor column. The reactor was then kept dry for 24 hours to allow the cells to adhere to the straw. The incubation without medium allows for the cells to adhere to the matrix to stabilize their location there so that they are not washed off in the presence of freshly added medium.

After 24 hours, fresh media was poured or recharged into the chamber containing the bioreactor column. The extracellular enzyme produced by the immobilized cells would be secreted into the media to be used for various applications.

After 12 hours, the culture media was decanted, and the chamber was charged with fresh media.

After every 12 hours, 1.5 ml of the decanted culture media was aliquoted into an eppendorf and 25 ml was aliquoted into falcon tube.

The production of protease and dehairing activity was checked using the decanted media after every 12 hours. 1.5 ml was used for protease quantification and 25 ml for dehairing.

Example 6

Enzyme Efficiency

Dehairing efficiency may be assessed by a number of different parameters. Main features of assessment were leather texture, increase in tensile strength and softness of hide. The suitability of the enzymes described herein over conventional chemical treatment may be assessed with regards to reusability, the time taken for completing the dehairing process, and effects on different parts of the hide (e.g., leather from neck, tail, leg area, for which dehairing can be a challenge), among others. The enzymes described herein were tested for dehairing goat and rabbit skin.

Figure 3:
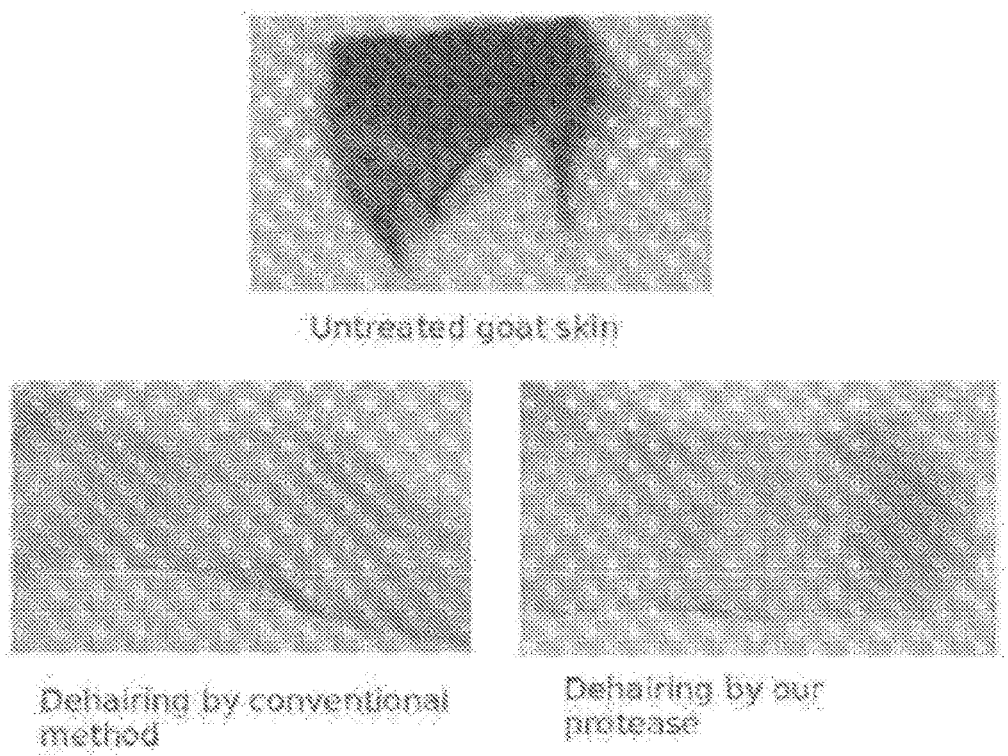
FIG. 3 provides illustrative photographs of a result of dehairing goat skin using protease from strain SRC002 (MTCC 5564) as compared with a conventional method of dehairing and with untreated goat skin.
Figure 4:
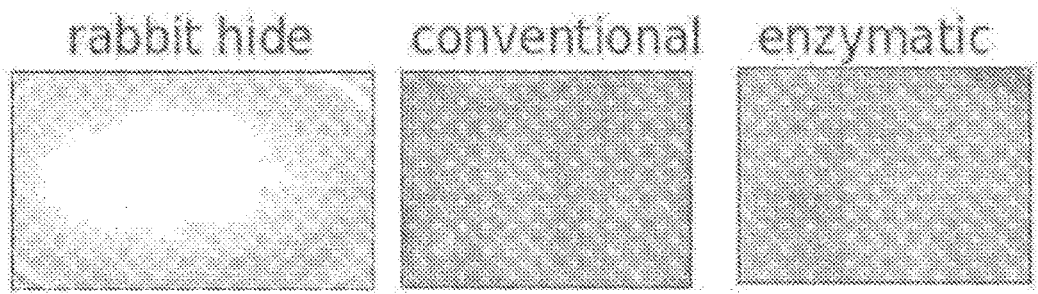
FIG. 4 provides illustrative photographs of a result of dehairing rabbit skin using protease from strain SRC002 (MTCC 5564) as compared with a conventional method of dehairing and with untreated rabbit skin.
Figure 5:
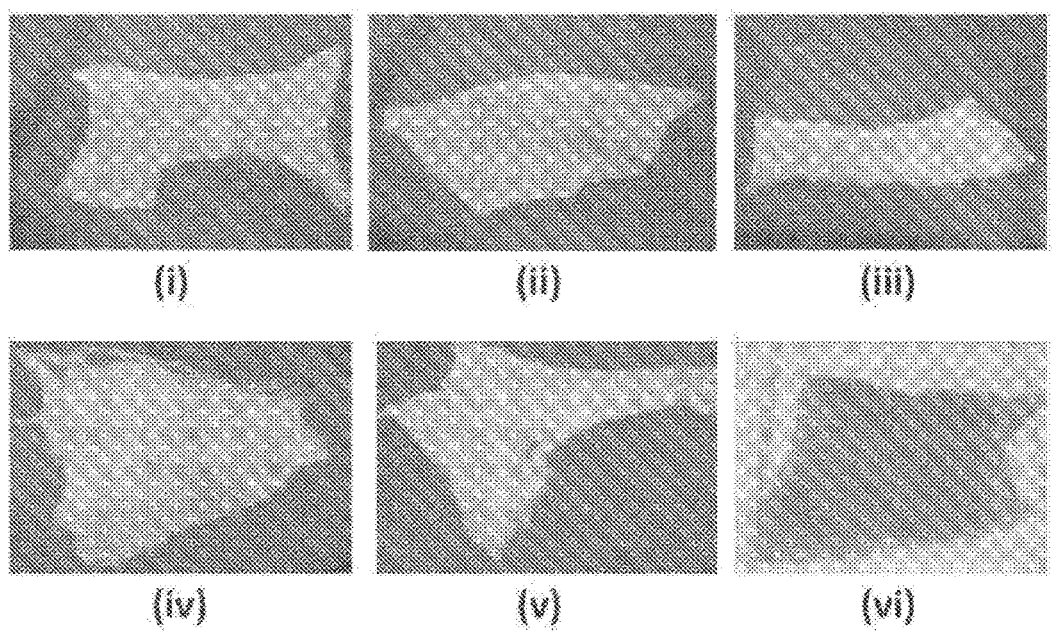
FIG. 5 provides illustrative photographs representing a comparative analysis of enzyme efficiency in dehairing. (i) Protease action (Strain A) in dehairing of goat hide collected from tail portion. (ii) Protease action (Strain A) in dehairing of goat hide collected from tail portion. (iii) Efficiency of lipase (Strain B) in dehairing of goat hide. (iv) Efficiency of protease along with lipase (Strain A+Strain B: 1:1) in dehairing of goate hid (tail portion). (v) Efficiency of protease along with lipase (Strain A+Strain B: 1:1) in dehairing of goat hide (leg portion). (vi) Dehairing efficiency by conventional process.
Figure 6:
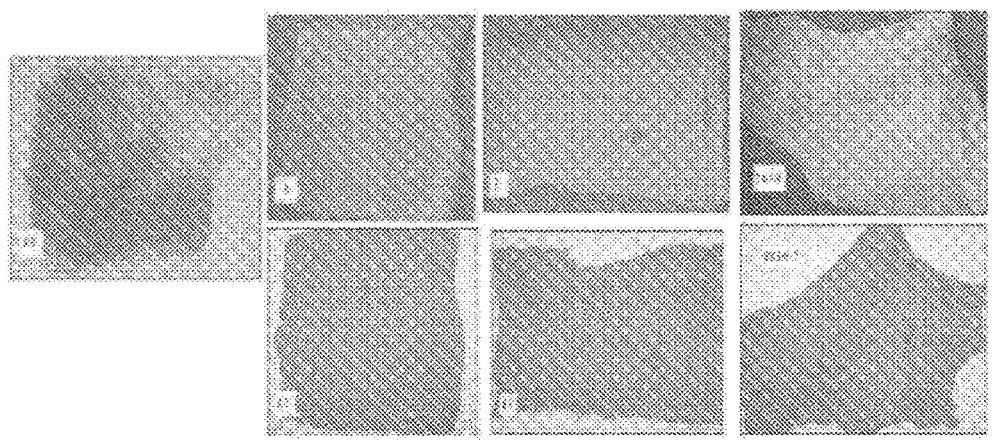
FIG. 6 provides illustrative photographs of a dehairing efficiency of the protease and the effect of tanning on dehaired hides. W-E represents the negative control (hide incubated with water without the treatment of the enzyme). C represents the hide treated in conventional chemical method (5% lime+ 5% sodium sulphide). E represents the enzyme treated hide. 2% L-E-T represents the enzyme treated hide with addition of 2% lime; the hides were incubated for 16 hours at room temperature. Mild, manual scrubbing results in removal of hair in all the cases. C-T, E-T, and 2% L-E-T represent the dehaired hides of conventional, enzymatic and combined treatment after tanning, respectively.

The efficiency of the enzymatic process for dehairing was analyzed by the relative increase in area and decrease in weight of the hides (Tables 1-3; FIGS. 3 and 4). For example, this may refer to the change in length and breadth of the hide pieces pre- and post-dehairing.

A lipase can decrease the fat content which can be measured as decrease in weight of the hide post treatment. Since lipases specifically degrade fat, they do not often affect or damage the leather itself. Lipases hydrolyze not only the fat on the outside of the hides and skins, but also the fat inside the skin structure. An advantage of using a lipase is to prepare leather with a uniform color and a cleaner appearance. Lipases also improve the production of hydrophobic (waterproof) leather. The combined action of lipase along with protease can provide a synergistic effect by facilitating proteolysis along with lipolysis.

At late log phase, both the cultures (bacterial cultures used for protease and lipase production) were collected, and were mixed in a 1:1 proportion in which hides were dipped. Protease activity of strain A was 37.5 units, lipase and protease activity of strain B were respectively 7.9 units and 38.1 units.

TABLE 1

Efficiency of protease enzyme in dehairing performed on hides from specific areas of body
Application of Protease

| Region of hide | Pre treatment | | | Post treatment | | |
| --- | --- | --- | --- | --- | --- | --- |
| | Length (in cm) | Breadth (in cm) | Weight (in gms) | Length (in cm) | Breadth (in cm) | Weight (in gms) |
| Back | 4.86 | 4.71 | 9.03 | 6.53 | 6.14 | 6.46 |
| Neck | 4.8 | 4.1 | 5.55 | 5.12 | 4.65 | 4.55 |
| Leg | 5.44 | 3.3 | 7.76 | 6.65 | 3.6 | 4.035 |

TABLE 1-continued

Efficiency of protease enzyme in dehairing performed
on hides from specific areas of body
Application of Protease

| Region of hide | Pre treatment | | | Post treatment | | |
|---|---|---|---|---|---|---|
| | Length (in cm) | Breadth (in cm) | Weight (in gms) | Length (in cm) | Breadth (in cm) | Weight (in gms) |
| Belly | 4.75 | 4.56 | 6.21 | 5.92 | 5.83 | 4.95 |
| Tail | 4.16 | 4.05 | 6.99 | 4.16 | 4.52 | 4.17 |

TABLE 2

Efficiency of conventional process in dehairing performed
on hides from specific areas of body.
Application of Conventional Process

| Region of hide | Pre enzyme treatment | | | Post enzyme treatment | | |
|---|---|---|---|---|---|---|
| | Length (in cm) | Breadth (in cm) | Weight (in gms) | Length (in cm) | Breadth (in cm) | Weight (in gms) |
| Back | 4.35 | 3.76 | 3.37 | 3.76 | 3.00 | 3.8 |
| Neck | 6.93 | 2.85 | 3.92 | 6.03 | 2.76 | 4.47 |
| Leg | 5.15 | 2.84 | 3.91 | 4.33 | 2.91 | 5.38 |
| Belly | 4.04 | 4.00 | 3.56 | 4.13 | 3.65 | 4.4 |
| Tail | 4.34 | 4.07 | 4.24 | 3.95 | 3.7 | 4.26 |

TABLE 3

Efficiency of combined protease and lipase action for dehairing
with respect to either protease or lipase.
Efficiency of the Combination of Protease and Lipase

| conditions | Pre treatment | | | | Post treatment | | | |
|---|---|---|---|---|---|---|---|---|
| | Length (in cm) | Breadth (in cm) | Thickness (in cm) | Weight (in gm) | Length (in cm) | Breadth (in cm) | Thickness (in cm) | Weight (in cm) |
| Application of protease from strain A | | | | | | | | |
| leg | 11.04 | 4.5 | 0.14 | 12.54 | 11.46 | 5.32 | 0.1 | 7.56 |
| neck | 8.84 | 3.86 | 0.46 | 11.25 | 10.15 | 4.34 | 0.15 | 7.9 |
| back | 11.54 | 4.06 | 0.35 | 13.85 | 13.37 | 5.34 | 0.15 | 8.40 |
| tail | 9.45 | 7.5 | 0.5 | 30.67 | 13.28 | 8.5 | 0.14 | 12.38 |
| Application of protease and lipase from strain B | | | | | | | | |
| Whole | 14.15 | 5.7 | 0.15 | 16.41 | 15 | 3.64 | 0.13 | 10.76 |
| Suspension | 11.50 | 5.74 | 0.29 | 15.70 | 14.8 | 4.4 | 0.14 | 11.73 |
| Application of both strains (1:1) | | | | | | | | |
| tail | 8.44 | 7.5 | 0.18 | 21.99 | 13.8 | 9.42 | 0.1 | 8.96 |
| Leg | 6.63 | 6.6 | 0.21 | 14.92 | 8.43 | 6.62 | 0.12 | 10.07 |
| Application of conventional process | | | | | | | | |
| | 8.4 | 5.6 | 0.15 | 12.27 | 7.4 | 5.54 | 0.25 | 12.25 |

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

The present disclosure is not to be limited in terms of particular embodiments described in this disclosure, which are illustrations of various aspects. Many modifications and variations can be made without departing from the spirit and scope of the disclosure, as will be apparent to those skilled in the art. Functionally equivalent methods and apparatuses within the scope of the disclosure, in addition to those enumerated herein, will be apparent to those skilled in the art from the foregoing descriptions. Such modifications and variations fall within the scope of the appended claims. The present disclosure is to be limited only by the terms of claims (e.g., the claims appended hereto) along with the full scope of equivalents to which such claims are entitled. It is to be understood that this disclosure is not limited to particular methods, reagents, compounds compositions or biological systems, which can, of course, vary. It is also to be understood that terminology used herein is for the purpose of describing particular embodiments only, and is not necessarily limiting.

With respect to the use of substantially any plural and/or singular terms herein, those having skill in the art can translate from the plural to the singular and/or from the singular to the plural as is appropriate to the context and/or application. Various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.).

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations).

Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.).

The term "about" as used herein refers to a value within 10% of the underlying parameter (i.e., plus or minus 10%), and use of the term "about" at the beginning of a string of values modifies each of the values (i.e., "about 1, 2 and 3" refers to about 1, about 2 and about 3). For example, a weight of "about 100 grams" can include weights between 90 grams and 110 grams. Further, when a listing of values is described herein (e.g., about 50%, 60%, 70%, 80%, 85% or 86%) the listing includes all intermediate and fractional values thereof (e.g., 54%, 85.4%). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

Thus, it should be understood that although the present technology has been specifically disclosed by representative embodiments and optional features, modification and variation of the concepts herein disclosed may be resorted to by those skilled in the art, and such modifications and variations are considered within the scope of this technology. As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments will be apparent to those skilled in the art. The various aspects and embodiments disclosed herein are for purposes of illustration and are not limiting, with the true scope and spirit of certain embodiments indicated by the following claims.

What is claimed is:

1. A rawhide dehairing process, comprising:
contacting a rawhide with a solution including a lipase and a protease for a predetermined amount of time, wherein the pH of the solution is from 5-10; and wherein the lipase is a *Pseudomonas aeruginosa* strain B/GZN secreted lipase; and removing hair from the rawhide.

2. A rawhide dehairing process, comprising:
contacting a rawhide with a solution including a *Pseudomonas aeruginosa* lipase and a protease for a predetermined amount of time, wherein the pH of the solution is from 5-10; and wherein the protease is a *Pseudomonas aeruginosa* strain A/SRC002 secreted protease; and removing hair from the rawhide.

3. The process of claim 1, wherein the protease is a bacterial protease.

4. The process of claim 1, wherein the protease is from a gram positive bacteria.

5. The process of claim 1, wherein the protease is from a gram negative bacteria.

6. The process of claim 3, wherein the protease is a *Pseudomonas aeruginosa* secreted protease.

7. The process of claim 6, wherein the protease is a *Pseudomonas aeruginosa* strain A/SRC002 secreted protease.

8. The process of claim 1, further comprising mechanically removing hair from the rawhide.

9. The process of claim 8, further comprising scrubbing the rawhide.

10. The process of claim 1, wherein the rawhide is contacted with the solution for 10 hours or more.

11. The process of claim 1, wherein the pH is about 7.5 to about 8.0.

12. The process of claim 1, wherein the pH is about pH 8.0.

13. The process of claim 1, wherein the solution comprises *Pseudomonas aeruginosa* strain B/GZN.

14. The process of claim 13, wherein the *Pseudomonas aeruginosa* strain B/GZN is immobilized or suspended in culture.

15. The process of claim 14, wherein the *Pseudomonas aeruginosa* strain B/GZN is immobilized in a porous matrix.

16. The process of claim 14, wherein the *Pseudomonas aeruginosa* strain B/GZN is immobilized in sodium alginate with calcium chloride.

17. The process of claim 1, wherein the rawhide is salted, dried, or both salted and dried.

18. The process of claim 1, wherein the solution is maintained at a temperature of about 40° C. for the predetermined amount of time.

19. The process of claim 1, wherein the solution is applied to the rawhide by one or more of painting, dipping or spraying.

20. The process of claim 1, wherein the solution is reusable.

21. The process of claim 20, wherein the solution is reusable for at least 7 cycles or at least 20 cycles.

22. The process of claim 2, wherein the lipase is a bacterial lipase.

23. The process of claim 2, wherein the lipase is from a gram positive bacteria.

24. The process of claim 2, wherein the lipase is from a gram negative bacteria.

25. The process of claim 22, wherein the lipase is a *Pseudomonas aeruginosa* secreted lipase.

26. The process of claim 25, wherein the lipase is a *Pseudomonas aeruginosa* strain B/GZN secreted lipase.

27. The process of claim 2, further comprising mechanically removing hair from the rawhide.

28. The process of claim 27, further comprising scrubbing the rawhide.

29. The process of claim 2, wherein the rawhide is contacted with the solution for 10 hours or more.

30. The process of claim 2, wherein the pH is about 7.5 to about 8.0.

31. The process of claim 2, wherein the pH is about pH 8.0.

32. The process of claim 2, wherein the solution comprises *Pseudomonas aeruginosa* strain A/SRC002.

33. The process of claim 32, wherein the *Pseudomonas aeruginosa* strain A/SRC002 is immobilized or suspended in culture.

34. The process of claim 33, wherein the *Pseudomonas aeruginosa* strain A/SRC002 is immobilized in a porous matrix.

35. The process of claim 33, wherein the *Pseudomonas aeruginosa* strain A/SRC002 is immobilized in sodium alginate with calcium chloride.

36. The process of claim 2, wherein the rawhide is salted, dried, or both salted and dried.

37. The process of claim 2, wherein the solution is maintained at a temperature of about 40° C. for the predetermined amount of time.

38. The process of claim 2, wherein the solution is applied to the rawhide by one or more of painting, dipping or spraying.

39. The process of claim 2, wherein the solution is reusable.

40. The process of claim 39, wherein the solution is reusable for at least 7 cycles or at least 20 cycles.

* * * * *

UNITED STATES PATENT AND TRADEMARK OFFICE
CERTIFICATE OF CORRECTION

PATENT NO.        : 8,524,481 B2
APPLICATION NO.   : 13/321316
DATED             : September 3, 2013
INVENTOR(S)       : Ray Chaudhuri et al.

It is certified that error appears in the above-identified patent and that said Letters Patent is hereby corrected as shown below:

On the Title Page, in Item (56), under "OTHER PUBLICATIONS", in Column 1, Line 1, delete "Chraterization of an Extracelluler" and insert -- Characterization of an Extracellular --, therefor.

On the Title Page, in Item (56), under "OTHER PUBLICATIONS", in Column 1, Line 3, delete "wetlans." and insert -- wetlands, --, therefor.

On Title Page 2, in Item (56), under "OTHER PUBLICATIONS", in Column 1, Line 1, delete "Iproving" and insert -- Improving --, therefor.

On Title Page 2, in Item (56), under "OTHER PUBLICATIONS", in Column 2, Line 16, delete "Chemistr," and insert -- Chemistry, --, therefor.

In the Specification

In Column 2, Lines 66-67, delete "bacterium" and insert -- bacterium. --, therefor.

In Column 3, Line 61, delete "goate hid" and insert -- goat hide --, therefor.

In Column 5, Line 67, delete "means" and insert -- means. --, therefor.

In Column 6, Line 59, delete "two ore more" and insert -- two or more --, therefor.

In Column 6, Line 61, delete "!:3:1, 1:3:2, 1:4:1, :1:4:2," and insert -- 1:3:1, 1:3:2, 1:4:1, 1:4:2,--, therefor.

In Column 7, Line 19, delete "55-70," and insert -- 55-70° C., --, therefor.

Signed and Sealed this
Sixth Day of May, 2014

Michelle K. Lee
*Deputy Director of the United States Patent and Trademark Office*

CERTIFICATE OF CORRECTION (continued)
U.S. Pat. No. 8,524,481 B2

In Column 8, Line 8, delete "55-70," and insert -- 55-70° C., --, therefor.

In Column 8, Line 30, delete "55-70," and insert -- 55-70° C., --, therefor.

In Column 9, Line 44, delete "Aeruginosa" and insert -- Aeruginosa. --, therefor.

In Column 10, Line 34, delete "gluteralolehyde" and insert -- glutaraldehyde --, therefor.

In Column 12, Line 13, delete "55-70," and insert -- 55-70° C., --, therefor.

In Column 13, Line 59, delete "mollasses" and insert -- molasses --, therefor.

In Column 14, Line 27, delete "100 by" and insert -- 100 bp --, therefor.

In Columns 15-16, under "Colony Morphology", in Line 2, delete "Isoate" and insert -- Isolate --, therefor.

In Column 17, Lines 66-67, delete "mollasses" and insert -- molasses --, therefor.